(12) United States Patent
Spies et al.

(10) Patent No.: US 7,771,718 B2
(45) Date of Patent: Aug. 10, 2010

(54) SOLUBLE MIC POLYPEPTIDES AS MARKERS FOR DIAGNOSIS, PROGNOSIS AND TREATMENT OF CANCER AND AUTOIMMUNE DISEASES OR CONDITIONS

(75) Inventors: Thomas Spies, Seattle, WA (US); Veronika Spies, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 667 days.

(21) Appl. No.: 10/512,181

(22) PCT Filed: Apr. 22, 2003

(86) PCT No.: PCT/US03/12299

§ 371 (c)(1),
(2), (4) Date: May 18, 2005

(87) PCT Pub. No.: WO03/089616

PCT Pub. Date: Oct. 30, 2003

(65) Prior Publication Data

US 2005/0233391 A1    Oct. 20, 2005

Related U.S. Application Data

(60) Provisional application No. 60/374,442, filed on Apr. 22, 2002.

(51) Int. Cl.
*A61K 39/395* (2006.01)
(52) U.S. Cl. ..................................... 424/130.1; 435/7.1
(58) Field of Classification Search ........................ None
See application file for complete search history.

(56) References Cited

U.S. PATENT DOCUMENTS

2004/0180002 A1 *  9/2004  Young et al. ................ 424/1.49

FOREIGN PATENT DOCUMENTS

WO    WO 98/19167    5/1998

OTHER PUBLICATIONS

Groh et al, PNAS, 2003, 100:9452-9457.*
Feldman et al, Nature, 2005, 435:612-619.*
Gura, Science, 1997, 278:1041-1042.*
Kaiser, Science, 2006, 313, 1370.*
White et al, Annu Rev Med 52:125-145, 2001.*
Norberto et al, Human Immunology, 1999, 60:323-330.*
Zou et al, Human Immunology, 2000, 61 (suppl 2) :S35.*
Freshney, Culture of Animal Cells, A Manual of Basic Technique, Alan R. Liss, Inc., 1983, New York, p. 4.*
Bauer et al., "Activation of NK cells and T cells by NKG2D, a receptor for stress-induced MICA," *Science*, 285(5428):727-729, 1999.
Chapman et al., "CD11b+CD28-CD4+ human T cells: activation requirements and association with HLA-DR alleles," *J. Immunol*, 157(11):4771-4780, 1996.
Das et al., "MICA engagement by human Vγ2Vδ2 T cells enhances their antigen-dependent effector function," *Immunity*, 15:83-93, 2001.
Feldman et al., "Perspectives of arterial gene therapy for the prevention of restenosis," *Cardiovasc. Res.*, 32(20:194-207, 1996.
Groh et al., "Tumour-derived soluble MIC ligands impair expression of NKG2D and T-cell activation," *Nature*, 419:734-738, 2002.
Groh et al., "Broad tumor-associated expression and recognition by tumor-derived γδ T cells of MICA and MICB," *Proc. Natl. Acad. Sci., USA*, 96:6879-6884, 1999.
Groh et al., "Cell stress-regulated human major histocompatibility complex class 1 gene expressed in gastrointestinal epithelium," *Proc. Natl. Acad. Sci., USA*, 93:12445-12450, 1996.
Groh et al., "Costimulation of CD8αβT cells by NKG2D via engagement by MIC induced on virus-infected cells," *Nature Immunology*, 2(3):255-260, 2001.
Groh et al., "Recognition of stress-induced MHC molecules by intestinal epithelial γδ T cells," *Science*, 279:1737-1740, 1998.
Ivashiv, "Cytokine expression and cell activation in inflammatory arthritis," *Adv Immunol*, 63:337-376, 1996.
Klavins et al., "Advances in biological markers for cancer," *Ann Clin Lab Sci*, 13:275-280, 1983.
Klimiuk et al., "Production of cytokines and metalloproteinases in rheumatoid synovitis is T cell dependent," *Clin Immunol*, 90:65-78, 1999.
Krause et al., "Rheumatoid arthritis synoviocyte survival is dependent on stat3," *J. Immunol*, 169:6610-6616, 2002.
Kurowska et al., "Fibriblast-like synoviocytes from rheumatoid arthritis patients express functional IL-15 receptor complex: endogenous IL-15 in autocrine fashion enhances cell proliferation and expression of Bcl-$x_L$ and Bcl-$2_1$," *J Immunol*, 169:1760-1767, 2002.
Lanier et al., "Turning on natural killer cells," *J Exp Med*, 191(8):1259-1262, 2000.
Lanier, "On guard-activating NK cell receptors," *Nat Immunol*, 2:23-27, 2001.

(Continued)

*Primary Examiner*—Misook Yu
*Assistant Examiner*—Mark Halvorson
(74) *Attorney, Agent, or Firm*—Fulbright & Jaworski L.L.P.

(57) ABSTRACT

The present invention provides prognostic and diagnostic methods for cancer, as well as methods for monitoring or staging cancer. Methods involve assaying for tumor-derived soluble MIC polypeptide—either MICA or MICB or both—in a sample from a subject. Assays can be implemented with a MIC polypeptide binding agent such as a MIC polypeptide antibody or recombinant NKG2D. An ELISA sandwich assay is employed in some embodiments of the invention to identify a soluble MIC polypeptide. In additional embodiments, a sample is assayed for tumor cell-surface bound MIC in addition to assaying for soluble MIC. The invention also provides methods of cancer therapy involving detecting cancer in the subject by assaying for soluble MIC polypeptide and then administering a cancer therapy.

14 Claims, 2 Drawing Sheets

OTHER PUBLICATIONS

Li et al., "Complex structure of the activating immunoreceptor NKG2D and its MHC class I-like ligand MICA," *Nat Immunol*, 2(5):443-451, 2001.

Martens et al., "Expansion of unusual CD4+ T cells in severe rheumatoid arthritis," *Arthritis and Rheumatism*, 40(6):1106-1114, 1997.

McInnes et al., "The role of interleukin-15 in T-cell migration and activation in rheumatoid arthritis," *Nat Med*, 2:175-182, 1996.

McInnes et al., "Interleukin-15 mediates T cell-dependent regulation of tumor necrosis factor-alpha production in rheumatoid arthritis," *Nat Med*, 3:189-195, 1997.

Mingari et al., "H7uman CD8+ T lymphocyte subsets that express HLA class I-specific inhibitory receptors represent oligoclonally or monoclonally expanded cell populations," *Proc. Natl. Acad. Sci., USA*, 93:12433-12438, 1996.

Moser et al., "CD94-NKG2A receptors regulate antiviral CD8+ T cell receptors," *Nature Immunology*, 3(2):189-195, 2002.

Muller-Ladner et al., "Molecular biology of cartilage and bone destruction," *Curr Opin Rheumatol*, 10:212, 1998.

Namekawa et al., "Functional subsets of DC4 T cells in rheumatoid synovitis," *Arthritis and Rheumatism*, 41(12):2108-2116, 1998.

Park et al., "Co-stimulatory pathways controlling activation and peripheral tolerance of human CD4+CD28- T cells," *Eur J Immunol*, 27:1082-1090, 1997.

Pohl et al., "Present value of tumor markers in clinic," *Cancer Detect Prevent*, 6:7-20, 1983.

Ravetech et al., "Immune inhibitory receptors," *Science*, 290:84-89, 2000.

Roberts et al., "Cutting edge: NKG2D receptors induced by IL-15 costimulate CD28-negative effector CTL in the tissue microenvironment," *J Immunol*, 167:5527, 2001.

Schmidt et al., "CD4+ CD7- CD28- T cells are expanded in rheumatoid arthritis and are characterized by autoreactivity," *J. Clin Invest*, 97:2027-2037, 1996.

Sikorska et al., "Clinical applications of carcinoembryonic antigen," *Cancer Detect Prevent*, 12:321-355, 1988.

Snyder et al., "Formation of the killer Ig-like receptor repertoire on CD4+CD28 null T cells," *J. Immunol*, 168:3839-3846, 2002.

Speiser et al., "CD28-negative cytolytic effector T cells frequently express NK receptors and are present at variable proportions in circulating lymphocytes from health donors and melanoma patients," *Eur J Immunol*, 29:1990-1999, 1999.

Steinle et al., "Interactions of human NKG2D with its ligands MICA, MICB, and homologs of the mouse RAE-1 protein family," *Immunogenetics*, 53(4):279-287, 2001.

Sultzeanu et al., "Human and cancer associated antigens: present status and implications for immunodiagnosis," *Adv Cancer Res*, 44:1-42, 1985.

Tieng et al., "Binding of *Escherichia coli* adhesin AfaE to CD55 triggers cell-surface expression of the MHC class I-related molecule MICA," *Proc. Natl. Acad. Sci., USA*, 99(5):2977-2982, 2002.

Vallejo et al., "Clonality and longevity of CD4+CD28null T cells are associated with defects in apoptotic pathways," *J Immunol*, 165:6301-6307, 2000.

Viriji et al., "Tumor markers in cancer diagnosis and prognosis," *Cancer*, 38:105-126, 1988.

Warrington et al., "CD4+,CD28- T cells in rheumatoid arthritis patients combine features of the innate and adaptive immune systems," *Arthritis and Rheumatism*, 44:13-20, 2001.

Wu et al., "An activating immunoreceptor complex formed by NKG2D and DAP10," *Science*, 285:730-732, 1999.

Yen et al., "Major histocompatibility complex class I-recognizing receptors are disease risk genes in rheumatoid arthritis," *J Exp Med*, 193:1159-1167, 2001.

Li et al., "A single amino acid substitution causes loss of expression of a MICA allele," *Immunogenetics*, 51:246-248, 2000.

Salih et al., "Cutting Edge: Down-Regulation of MICA on Human Tumors by Proteolytic Shedding," *J. Immunol.*, 169:4098-4102, 2002.

Doubrovina et al., "Evasion from NK cell immunity by MHC class I chain-related molecules expressing colon adenocarcinoma," *The Journal of Immunology*, 171:6891-6899, 2003.

Supplementary European Search Report, issued in European Application No. 03721800, dated Dec. 19, 2008.

* cited by examiner

SEQUENCE LISTING

```
<160> NUMBER OF SEQ ID NOS: 10

<210> SEQ ID NO 1
<211> LENGTH: 11722
<212> TYPE: DNA
<213> ORGANISM: Homo sapiens

<400> SEQUENCE: 1
cactgcttga gccgctgaga gggtggcgac gtcggggcca tggggctggg cccggtcttc      60
ctgcttctgg ctggcatctt ccctttttgca cctccgggag ctgctgctgg tgagtggcgt    120
tcctggcggt cctcggcgga gcgggagcag tgggacgttt ccggggggtcg ggtgggtagc    180 ggcgagcgct gtgcggtcag ggcggggctc ctgtgccctg tcggtggcgc agggagctgg    240
acgcggcccg ttaccgccac acttcagccc tgcttccccg tcacttttca gtcctcctcg    300
ggatcgcgca tcacctgcac tttctggtct cctcctgctc tttctctcct cgcgtctcct    360
ccgcttcctc tcactttcg gacaaaccag tccttctgag gcccatgggt tcccgggctg     420
cctccggggc tgctcctgtg aatggcattc gagtgccctt ccagcgcggc cactgaagca    480
gccacaaccc ccggtgctcg gggcggctct caggtccctg aagtcctgtc ctctcccgga    540
gccgacgtgt tctcagctcc tgggccgcag ctcctggagt aggggccctc ctttctcggg    600
acccggagct ggtgcttcct gctgctgtgg ggactgtggg gggtcctgac tctcaagctg    660
aggggttgga gtctgcaggc tccgggcaga ggattcttcc tgcgacttct ctcatcccca    720
gctcattctc ccctcgcctc tggctccgag ggtcctctcc tctctctcat cccacccta    780 ctaatgacca gtgatctaag gacaccagat tccctctcac ctcctccctg cccatctcag    840
ggcccgctga gtccttttgc cctcccagct ccctgctacc ccttcctgtg tgctgttctc    900
tgatccattt ctagggtgtc ctctgccctc atccctgtc cccgccaccg aagtcctcc     960 tgcacccctt atgggccttt cctacaagca gccttcaccc agtgctgccc ctatgcctcc   1020
ccgttcccaa atgtccctga ctctaacttt ctggtgctgc cttttatccg gggggtctt    1080
```

-continued

```
ccctccatcc cactcccctc cagaccccca aggggaaccc tgatgctaat ggcagttggg    1140
ccttaggcag ggcgcagggc agcgcagatg cccctcccc  tccagtgcag atgcctgttc    1200
tggaccctgc ctcattgtgg cccttcccc  actccttcat cctcagcctc accctcttga    1260
ggacccacc  ctccagccca caggtgctgg accatccctc cctggtccct ccgcccctct    1320
ccaccttggg accttgtgct gctcctatct cttgcccagc tgccttgggc cctcagcacg    1380
ttctcatctt tcagtgggaa agtgggagtg ctggagcata tgacagtgct gagcatcttt    1440
cccaagcccc accctccccc agagcaccct ccctcctgt  cctcaccta  ccaagttc     1500
tcccacagtc actcctgccc catgctcatg ccgccctcca gttcttgctc tgcccatctc    1560
ccctccccaa cccagaccta aacaggctg  ttgggccaac tgttccttga ccttccttct    1620
tttcttttgg ttccttgacc ccagtgggct ctcactcccc acccgcata  tctaaaatct    1680
gttttgcctg ctcttggggt gccactgctc ccctccagc  attactcctt ttggcaggtc    1740
cttcctcagg ctgagaatct cccctctac  cttggtttc  tctctctggc cagcaccccc    1800
actccttgct ttgttttaa  ttttaactt  ttgtttgggt acgtagtaga tatatatgta    1860
tatatttatg gggtacatgg gatattttga cacaggccta caatatgtaa taatcacatc    1920
agggtaaatg ggttatatca caacaagcat ttatccttc  tttgtgctac aaacaatccc    1980
attatgctct ttcagttatt tttaaatgta caataaatta ttgttgactg tactcaccct    2040
gctgtgctat ctactagatc ttattcattc taattatatt tttgtaccca ttattaacca    2100
tccctgctcc cccactcccc actacccttc tcagcctctg gtaatcatca ttctattgtc    2160
tctcccatg  aggtccattg ttttaaattt tggctgccac aaataagtga aacatgcaa     2220
agtttgtctg tctgggcctg gggcttattt cacttcacag gatgacctcc agttctttgc    2280
aaatgacacg atggctgaat agttctccac atacacatgt acaccacatt ttctttatcc    2340
atgcgtctgt tgatggacac ttagattgct tgcagatctt ggctactttg aatagtgctg    2400
caataaacat ggaaaagtag atagctcttt aatataccga tttcctttct ttggagtata    2460
tgcctaacag tgggagtgct ggagcatatg acagctctat tgtatttta  gttttggaa     2520
gaacctccac attgtttccc atagtggttg tactagttta cgttcccacc aacagtgtac    2580
atcctcacca gcattcctta tttctacatc ctcgccagca ttccttattg cctgtcttct    2640
ggataaaagc cagtttatct ggggtgggat gttatctcgt aggagttttg atttgccttc    2700
atctgttgac gaatgatgtt gagcaccttt tcatataccct gtttgccatt tatatgtctt    2760
cttttgagaa atgactattc agatctttc  tcattttaa  attggattat tatattttt    2820
ttcctatagt tgttcgagct ccttatatgt ttcagttact gatcctttgt cagatgaata    2880
gtttgaaaat attttctccc attcttggat ggtctcttca ttttgtttat tgtttccttt    2940
gctgtgcaga agccttttta cttgatatga tcccatttat gcaattttac tttggttacc    3000
tgtgcttgtg gggtattact ttaaaaatct ttgcccagtc caatatccta gagagtttcc    3060
ccaatgtttt cttgtatagt ttcatagttt gaggtcatag atttacatct ttaatccact    3120
ttgatttgat ttttgtatat ggtgaaagac agggtctagt ttcattcttc tgcataagga    3180
tatctagttt cccagcacc  attttttgaag agactctcct ttgccaatgt gtgttcttgg    3240
tacctttgtt ggaaatgagt ttactgtaga tgtatggaat tgtttctggg ttctctattc    3300
tgtttcattg gtctgtgtgt ctgttttat  gccagtatca tgctgtttg  gttactgtag    3360
ctctgtagta taatttgaag tcagataatg tgattcctct agttttgttc attttgctca    3420
```

```
ggatagcttt atctattctg gtttttttgt ggttccatat gcattttagg attattttta    3480
ttatttctgt gaagaatgtc attagtgttt tgatagggat tgcattgaat ctgtagatta    3540
ctttgggtag tatggatatt tcaacaaaac tgattcttcc aatccatgaa cgtggactat    3600
cttttccatt ttttgtgtcc ttcaattttt tgcatcagtg ttttttgttt ttggtttttg    3660
agatggagtt tcactcttgt tgcccaggct agaatgcaag ggtgtgatct tggctcaccg    3720
caacctccgc ctcccaggtt caagctattc ttctgcctca gcctcccaag tagctgggat    3780
tacaggcatg tgccactgtg cctggctaat tttctatttt tattagagat ggggtttctc    3840
tatgttggcc aggctagtct tgaactcctg acctcaggtg atccacctgc ctcggcctcc    3900
caaagtgctg ggattacagg catgagccac cacgcccagc cacatcactg ttttatagtt    3960
tttattggag aggtctttca cttcttcagt taggtttatt cctcagtatt ttattttatt    4020
tgtagctatt gtaaatggga ttcgtttctt gatttctttt tcagattatt gctgttagc     4080
actgattttt gcatgttgat tttgtatcct gcaactttac tgaatttgtt cttcagttct    4140
aatggttttt tggtggagtc tttaggtttt tccaaatatc agaccacatg atctgcaaac    4200
aaggataatt tgacttcttc ttttccagtt ttaatgccct ttctttcttt ctcctgtctg    4260
attgctctag ttaggatctg cagtactgtg ttgcataact gtggtaaaat tagtcatcct    4320
tgtcttattc cagatcttag agaaaaggct ttcagttttc ccccattcag tatgttacta    4380
gctgtgagtt tgtcatatat ggcttttatt atattgaggt ctgttccttg tatacttagt    4440
tttttgagag ttttttatcat gaagggatgt tgaatttatc aaatgctttt tcagtatcaa    4500
ttgaatgata ctggcttttg tcctttattc tgttgatatg acgtattaca ttgattgatt    4560
tgtgtatgtt aaatcatcct tgcatacctg gaatacattc cacttgctca taagaatga     4620
tctttttttaa tgtattgttg aatgtggttt gctagtattt ccttgacgat ttttgcatcg    4680
gtgttcatca gggatatagg cctgtagttt tctttttttat gatgtgtctt tgcctggttt    4740
ttgtatcagg atattcctgg cttttgtaaaa tgagtttgga agtattccct cctcctctat    4800
ttttcagaac agtttgaata ggactgacat atgttgttct ttaaaagttt aattgtggta    4860
aattatacat tacataaatt ttactgtttt aaccacttttt aagtgtatac tcggtggcat    4920
tagatacatt cacattttttg tgcaacccaa aactctgtgc ccattaatcg gtaactcccc    4980
attcctccct acctctggcc cctggtaacc accattctac ttttttgtttc tatgaatttg    5040
accactctag gtacctcatt taagcagaat catgtaatgt ttgtcttttt gtttctggct    5100
tatttcactt ataatatttt tgaggttcgg tgggcacagt ggctcacgcc tggatttcca    5160
gcactttggg aggctgaagc aggtggatca cctgagtttc ggagttcgaa accagcctgg    5220
ccaacatggt gaaaccccat ctctactaaa aataataaaa gttagccggg cgtgatggcg    5280
ggtgcctgta atcccaacta cttgggaggc tgaggcagga gaatcgcttg aatccgggaa    5340
gtggaggttg cagtgagctg agatcaggcc actgcactcc agcctgggca acaagagtga    5400
aattccatct ccaaaaaaaa aaaataaaac aataataata ataatatttt tgaggttcat    5460
ccaagttgta gtatgggtca gaatttcatt ccttttaagg atggataata ctcattatat    5520
gtatgtacca catcttggtt atccatccct cagacaatgg acacttgggt tacttctacc    5580
ttttggatat tggcaaatat ttcatttcct ttgggtatat atttatttcc tttgggtatt    5640
tcttttgggt atatatccag aaatagaagc agtacacagg ggcttcattt tctctgtctc    5700
tttgccaacc ttgctctgtg tgtgtgtgta tgtgtgtgtg taggtgtgtg ataacagcca    5760
tcctgattgg tttcaggtgg catctcattg tggtttggat ttgcattttc ctaatgagtg    5820
```

```
ctgatattga gcatcttttc atgtgtttgt tgatcatttg taattttctt tgaagaattg    5880
gccatttaag tcttttgccc attttttccc ccacatagct tctcttatca gatatatgac    5940
ttgcaatatt tatttcattt cggggttgat tgcttttca ctctgattgt gcccttgat     6000
gcatagatgt tttgaatttt catcagtcta ctttgtcagt tctttctatt ctatctgtgc    6060
tttggtgtca tatccatgaa agcactgtca aatcctatgt catgaacatt atccccaatg    6120
tttgcttcta agaaattttt aggttttagt tcttgagtgt agagtttagg tctttgattc    6180
attttgagtt aatttttgta tatagtgcaa attaagggtc caattttatt ttaacacccc    6240
ctgcccccag aactatttgc tgaaaagatc aactgactct ttgtcacctg ctcacccag    6300
tggacactag ctgttccatc caattgctgt cctgggcct tgtcatgcta ctcttccact    6360
ttgaacccaa gcccacaccg ttcgttgctc ccctctggga tactgacccc actataaact    6420
tctctgggc tacaaccttc ctacccttg tgcctcatga ccaccccctc ccttgtcccc    6480
gccatgccca tgatgagtct cttctcgagg cagctcccct tgcctccatc tcaccctcag    6540
cctatgcacc acagccacac tggacatggg tccctgtgag cctgagtccc ttcccattcc    6600
caccatctcc tctggcaaga ccttccttcc accaccttca tgctcctccc ttgccctgc    6660
agggcagcct ctccccttgg cccctattcc cttaggggc ttgtggccac ccagtccttg    6720
cacctggcct acaagtttgc catcttcatt ccccttctt ctgttcatca gcccctcct    6780
ctatcctccc ccctcacag tttctttgt atatgaaatc tcgttcttg tccctttgcc    6840
cgtgtgcatt tcctgcccca ggaaggttgg gacagcagac ctgtgtgtta aacatcaatg    6900
tgaagttact tccaggaaga agtttcacct gtgatttcct cttccccaga gccccacagt    6960
cttcgttata acctcacggt gctgtcctgg gatggatctg tgcagtcagg gtttcttgct    7020
gaggtacatc tggatggtca gcccttcctg cgctatgaca ggcagaaatg cagggcaaag    7080
ccccagggac agtgggcaga agatgtcctg ggaaataaga catgggacag agagaccagg    7140
gacttgacag ggaacggaaa ggacctcagg atgaccctgg ctcatatcaa ggaccagaaa    7200
gaaggtgaga gtcggcaggg gcaagagtga ctggagaggc cttttccaga aaagttaggg    7260
gcagagagca gggacctgtc tcttcccact ggatctggct caggctgggg gtgaggaatg    7320
ggggtcagtg gaactcagca gggaggtgag ccggcactca gcccacacag ggaggcatgg    7380
gggagggcca gggaggcgta ccccctgggc tgagttcctc acttgggtgg aaaggtgatg    7440
ggttcgggaa tggagaagtc actgctgggt ggggcaggc ttgcattccc tccaggagat    7500
tagggtctgt gagatccatg aagacaacag caccaggagc tcccagcatt tctactacga    7560
tggggagctc ttcctctccc aaaacgtgga gactgaggaa tggacagtgc cccagtcctc    7620
cagagctcag accttggcca tgaacgtcag gaatttcttg aaggaagatg ccatgaagac    7680
caagacacac tatcacgcta tgcatgcaga ctgcctgcag gaactacggc gatatctaga    7740
atccagcgta gtcctgagga agagggtac ggacgctggc caggggctct cctctccctc    7800
caattctgct agagttgcct cacctccaag atgtgtccag ggaaaccctc cctgtgctat    7860
ggatgaaggc atttcctgtt ggcacatcgt gtcctgattt tcctctattg ttagagccac    7920
tggataaaga cagtgggtca gggactggac catccagtgt tgtaatcagg gcaagtagag    7980
gaccctccga cagaatcctg agcctgtggt gggtgtcagg caggagagga agccttcagg    8040
gccagggctg cccctctgc ctcccagcct gccatcctg gagagttccc tcctggccc    8100
acaacccagg agtccacccc tgacatcccc ctcctcagca tcaatgtggg gatcccagag    8160
```

```
cctgaggcca cagtcccaag gcccatcctc ctgccagcct ggaagaactg ggccccagag   8220
tgaggacaga cttgcaggtc aggggtcccg gagggcttca gccagagtga aacagtgaa    8280 gagaaacagc cctgttcctc tcccctcctt agagggagc agggcttcac tggctctgcc    8340
ctttcttctc cagtgccccc catggtgaat gtcacccgca gcgaggcctc agagggcaac   8400
atcaccgtga catgcagggc ttccagcttc tatccccgga atatcacact gacctggcgt   8460
caggatgggg tatctttgag ccacgacacc cagcagtggg gggatgtcct gcctgatggg   8520
aatggaacct accagacctg ggtggccacc aggatttgcc aaggagagga gcagaggttc   8580
acctgctaca tggaacacag cgggaatcac agcactcacc ctgtgccctc tggtgagcct   8640
agggtgaccc tggagagggt caggccaggg tagggacagc agggatggct gtggctctct   8700
gcccagtgta taacaagtcc cttttttca gggaaagtgc tggtgcttca gagtcattgg    8760
cagacattcc atgtttctgc tgttgctgct gctgctgctg ctattttgt tattattatt    8820 ttctatgtcc gttgttgtaa gaagaaaaca tcagctgcag agggtccagg tgagaaaagc   8880
gggcagtttc tggagatggt aaggcccctg tctgggcagt agggtcccct cattgctcct   8940
gcaaagatag gcatgttggt gacaaggctt ctgtaacagg ggatgaaagt tgggaatttt   9000
gggaagggaa tgggggcagc atctccatct acacccataa gtgctgccca gcgagggtc    9060 aaacgcccag ctgtggcatc ttcctgctgc aggtgaggag tgggcagcag ggagggctgc   9120
ggcgcctgct ctgtccccat cccggtctct gtgtctcttg gactcactag ggcgcatcca   9180 ggtgggggtga ctgggaatc acgtgctgaa tgctgagggc ctggatgatc acggcctcag   9240
agggagcaaa tagtaaaggc agctgtgatc tggggagggc cagaaactgg agaggaatct   9300
gaggagaggc ggtgccccta ttcccttcct ctctgcatcc ccctcccctg tttctccagc   9360
catcggggcg gacaccgaga aaaagaccta tgaggcccag cctgggggcc ctgcctgtgt   9420
agcccttggg agaccctag taacaggag ggtcctgagc acacatggcc atctctgtcc     9480
actgtgcagc tccccatgca cctcctccag gagctttctt ggggttgtcg tgtcctctgc   9540
accattcgag gccctactct ttccaggttc ccacggcctg gcctccctga gtttcttgca   9600
gatgacatgg atgagtagat aagcagatgt ccctgggcca tttgaggagt ggggcccagc   9660
ccctcatcag ggcagctgtg gtccctgttt tcatcctacc tccgagtgtt ttcttctcca   9720
gtccctgagg gacacagtcc tcagggccca tgttttgg gatttaatct gtgctctgtg     9780
gcctcacctt gccttccctg agccaatttc cctttctaaa ggtggtcact gcctggtaag   9840
tttggagtaa gggacggtca gaatcatttc ccctacagtc aggttgtttg atgggggatg   9900
aaaagagaca gcaggaagtt ttgtgttctct gcaaagacag aagcagttca ggcgacagta   9960
agaggctggg gtgtccagga gggtgtgtct ggcagtaggg tcgctggttt ctcatccttg   10020
aacctaattg cactgtcagt cggcccctca ggcctgagca gatgggaagg tttgtcccct   10080
gccctgcagc aagagggccc tgtccaggag gcacccacaa cagaggcagt gcaggtctgt   10140
ggtcactcct actctcacct gtggcgtctc ccgtagaggg attgtcagtt ctggttccct   10200
gtgggcagga atggtttcct cataggtcac tggagttttg gccaggaaaa gagtatgaag   10260
ttcatgtggc agtttctcaa aattcctgct ttcaatgttg atgtccagta aagatattcg   10320
taatttcagc tctataatct taataggatt tcctctaata ttgtgaagca tattatatga   10380
aacaggaaca caaatttctc aaaattcctg cgatgtccaa taaagatttt cataatttca   10440
gctctgcaat cttaatagga tttcctaata ctgtaaagca tattaaatga aacaggaact   10500
caaatttgga gcccctctc caggaggttc tgtgtggaga tggtggctgt ggcagtggca   10560
```

-continued

```
gttcccaggt gcagagggtg ggcagaggca gcctcaggct aaggggtctc ccctactcca    10620
catggagaaa atcccttgta ggttgcaagg gcagtggccg ggtggaatcc ctgctaggga    10680
cagagcagga aggcctcgca gcctcaccaa gcagcagccc tggggtggag ctgcgtttcc    10740
agggttaagc ggaccaggca ggagtagcgg ttactcaaga gcaggtcaca ggcttgggtt    10800
gtgagggtca ggagaggcca ggcctcctcg agcaaggtgg gggtcccagg gtcaggtcag    10860
gtgcagatcc tgtggcagcc acgtctttcc atgctgggcc tgctgggccc cccaggcttc    10920
ctgatggggt ccccagttag gagctgcctg ctcaggggtg ggaggggagg agcactgagc    10980
tgcagataga gggcagagcc cacagtgggc agggcctgcc ctggtgtgta ggtgcctctg    11040
caggagagga gggcctgggg actgagagca agggtcaggg cctctctttg ggaggcctc     11100
tcactgtaac aggactggtc aggcctgaga ggagggcact gggttccctc ttgggtcttg    11160
tcctttagtc ttggggcct ttccctccct gcacgatgag tggtgggcac agggcacggg     11220
ctgatgttga tggagtgatg ggagggaact ggcagggct gggaaaagca aggagggagg     11280
aagaaaaaag tgggggcctc atcttccctc agagaaaggg caaatctggt tttggagcaa    11340
ctgaagagag aaaagtcccc agggaataaa cacaacactg cacccagtgg agcatttacc    11400
catttccctc ttttctccag agctcgtgag cctgcaggtc ctggatcaac acccagttgg    11460
gacgagtgac cacacaggatg ccacacagct cggatttcag cctctgatgt cagctcttgg   11520
gtccactggc tccactgagg gcgcctagac tctacagcca ggcggctgga attgaattcc    11580
ctgcctggat ctcacaagca ctttccctct tggtgcctca gtttcctgac ctatgaaaca    11640
gagaaaataa aagcacttat ttattgttgt tggaggctgc aaaatgttag tagatatgag    11700
gcatttgcag ctgtgccata tt                                             11722
```

<210> SEQ ID NO 2
<211> LENGTH: 385
<212> TYPE: PRT
<213> ORGANISM: Homo sapiens

<400> SEQUENCE: 2

```
Met Gly Leu Gly Pro Val Phe Leu Leu Leu Ala Gly Ile Phe Pro Phe
  1               5                  10                  15

Ala Pro Pro Gly Ala Ala Ala Glu Pro His Ser Leu Arg Tyr Asn Leu
             20                  25                  30

Thr Val Leu Ser Trp Asp Gly Ser Val Gln Ser Gly Phe Leu Ala Glu
         35                  40                  45

Val His Leu Asp Gly Gln Pro Phe Leu Arg Tyr Asp Arg Gln Lys Cys
     50                  55                  60

Arg Ala Lys Pro Gln Gly Gln Trp Ala Glu Asp Val Leu Gly Asn Lys
 65                  70                  75                  80

Thr Trp Asp Arg Glu Thr Arg Asp Leu Thr Gly Asn Gly Lys Asp Leu
                 85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Val Glu Thr Glu Glu Trp Thr Val Pro Gln Ser Ser Arg Ala Gln Thr
145                 150                 155                 160
```

```
Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Glu Ser Ser Val Val Leu Arg Arg Val Pro Pro Met
        195                 200                 205

Val Asn Val Thr Arg Ser Glu Ala Ser Glu Gly Asn Ile Thr Val Thr
    210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ala
305                 310                 315                 320

Ala Ile Phe Val Ile Ile Ile Phe Tyr Val Arg Cys Cys Lys Lys Lys
                325                 330                 335

Thr Ser Ala Ala Glu Gly Pro Glu Leu Val Ser Leu Gln Val Leu Asp
            340                 345                 350

Gln His Pro Val Gly Thr Ser Asp His Arg Asp Ala Thr Gln Leu Gly
        355                 360                 365

Phe Gln Pro Leu Met Ser Ala Leu Gly Ser Thr Gly Ser Thr Glu Gly
    370                 375                 380

Ala
385

<210> SEQ ID NO 3
<211> LENGTH: 2380
<212> TYPE: DNA
<213> ORGANISM: Homo sapiens

<400> SEQUENCE: 3
gggccatggg gctgggccgg gtcctgctgt ttctggccgt cgccttccct tttgcacccc     60
cggcagccgc cgctgagccc cacagtcttc gttacaacct catggtgctg tcccaggatg    120
aatctgtgca gtcagggttt ctcgctgagg acatctggga tggtcagccc ttcctgcgct    180
atgacaggca gaaacgcagg gcaaagcccc agggacagtg gcagaagat gtcctgggag     240 ctaagacctg ggacacagag accgaggact tgacagagaa tgggcaagac ctcaggagga    300
ccctgactca tatcaaggac cagaaaggag gcttgcattc cctccaggag attagggtct    360
gtgagatcca tgaagacagc agcaccaggg gctcccggca tttctactac gatggggagc    420
tcttcctctc ccaaaacctg gagactcaag aatcgacagt gccccagtcc tccagagctc    480
agaccttggc tatgaacgtc acaaatttct ggaaggaaga tgccatgaag accaagacac    540
actatcgcgc tatgcaggca gactgcctgc agaaactaca gcgatatctg aaatccgggg    600
tggccatcag gagaacagtg cccccatgg tgaatgtcac ctgcagcgag gtctcagagg    660
gcaacatcac cgtgacatgc agggcttcca gcttctatcc ccggaatatc acactgacct    720
ggcgtcagga tggggtatct ttgagccaca cacccagcgt gggggat gtcctgcctg      780
```

-continued

```
atgggaatgg aacctaccag acctgggtgg ccaccaggat tcgccaagga gaggagcaga    840
ggttcacctg ctacatggaa cacagcggga atcacggcac tcaccctgtg ccctctggga    900
aggtgctggt gcttcagagt caacggacag actttccata tgtttctgct gctatgccat    960
gttttgttat tattattatt ctctgtgtcc cttgttgcaa gaagaaaaca tcagcggcag   1020
aggtccaga gcttgtgagc ctgcaggtcc tggatcaaca cccagttggg acaggagacc    1080
acagggatgc agcacagctg ggatttcagc tctgatgtc agctactggg tccactggtt    1140
ccactgaggg cgcctagact ctacagccag gcggccagga ttcaactccc tgcctggatc   1200
tcaccagcac tttccctctg tttcctgacc tatgaaacag aaataacat cacttattta    1260
ttgttgttgg atgctgcaaa gtgttagtag gtatgaggtg tttgctgctc tgccacgtag   1320
agagccagca aagggatcat gaccaactca acattccatt ggaggctata tgatcaaaca   1380
gcaaattgtt tatcatgaat gcaggatgtg ggcaaactca cgactgctcc tgccaacaga   1440
aggtttgctg agggcattca ctccatggtg ctcattggag ttatctactg ggtcatctag   1500
agcctattgt ttgaggaatg cagtcttaca agcctactct ggacccagca gctgactcct   1560
tcttccaccc ctcttcttgc tatctcctat accaataaat acgaagggct gtggaagatc   1620
agagcccttg ttcacgagaa gcaagaagcc ccctgacccc ttgttccaaa tatactcttt   1680
tgtctttctc tttattccca cgttcgccct tgttcagtc caatacaggg ttgtggggcc    1740
cttaacagtg ccatattaat tggtatcatt atttctgttg ttttgtttt tgttttgtt    1800
tttgtttttg agacagagtc tcactcgtca cccaggctgc agttcactgg tgtgatctca   1860
gctcactgca acctctgcct cccaggttca agcacttctc gtacctcaga ctcccgatag   1920
ctgggattac agacaggcac caccacaccc agctaatttt tgtattttt gtagagacgg    1980
ggtttcgcca agttgaccag cccagtttca aactcctgac ctcaggtgat ctgcctgcct   2040
tggcatccca aagtgctggg attacaagaa tgagccaccg tgcctggcct attttattat   2100
attgtaatat attttattat attagccacc atgcctgtcc tatttttctta tgttttaata  2160
tattttaata tattacatgt gcagtaatta gattatcatg ggtgaacttt atgagtgagt   2220
atcttggtga tgactcctcc tgaccagccc aggaccagct ttcttgtcac cttgaggtcc   2280
cctcgccccg tcacaccgtt atcgattact ctgtgtctac tattatgtgt gcataattta   2340
taccgtaaat gtttactctt taaataaaaa aaaaaaaaaa                         2380
```

<210> SEQ ID NO 4
<211> LENGTH: 383
<212> TYPE: PRT
<213> ORGANISM: Homo sapiens

<400> SEQUENCE: 4

```
Met Gly Leu Gly Arg Val Leu Leu Phe Leu Ala Val Ala Phe Pro Phe
  1               5                  10                  15

Ala Pro Pro Ala Ala Ala Glu Pro His Ser Leu Arg Tyr Asn Leu
             20                  25                  30

Met Val Leu Ser Gln Asp Glu Ser Val Gln Ser Gly Phe Leu Ala Glu
         35                  40                  45

Gly His Leu Asp Gly Gln Pro Phe Leu Arg Tyr Asp Arg Gln Lys Arg
     50                  55                  60

Arg Ala Lys Pro Gln Gly Gln Trp Ala Glu Asp Val Leu Gly Ala Lys
 65                  70                  75                  80

Thr Trp Asp Thr Glu Thr Glu Asp Leu Thr Glu Asn Gly Gln Asp Leu
                 85                  90                  95
```

```
Arg Arg Thr Leu Thr His Ile Lys Asp Gln Lys Gly Gly Leu His Ser
                100                 105                 110

Leu Gln Glu Ile Arg Val Cys Glu Ile His Glu Asp Ser Ser Thr Arg
            115                 120                 125

Gly Ser Arg His Phe Tyr Tyr Asp Gly Glu Leu Phe Leu Ser Gln Asn
        130                 135                 140

Leu Glu Thr Gln Glu Ser Thr Val Pro Gln Ser Ser Arg Ala Gln Thr
145                 150                 155                 160

Leu Ala Met Asn Val Thr Asn Phe Trp Lys Glu Asp Ala Met Lys Thr
                165                 170                 175

Lys Thr His Tyr Arg Ala Met Gln Ala Asp Cys Leu Gln Lys Leu Gln
            180                 185                 190

Arg Tyr Leu Lys Ser Gly Val Ala Ile Arg Arg Thr Val Pro Pro Met
        195                 200                 205

Val Asn Val Thr Cys Ser Glu Val Ser Glu Gly Asn Ile Thr Val Thr
        210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asn Thr Gln Gln Trp Gly Asp Val
                245                 250                 255

Leu Pro Asp Gly Asn Gly Thr Tyr Gln Thr Trp Val Ala Thr Arg Ile
            260                 265                 270

Arg Gln Gly Glu Glu Gln Arg Phe Thr Cys Tyr Met Glu His Ser Gly
        275                 280                 285

Asn His Gly Thr His Pro Val Pro Ser Gly Lys Val Leu Val Leu Gln
        290                 295                 300

Ser Gln Arg Thr Asp Phe Pro Tyr Val Ser Ala Ala Met Pro Cys Phe
305                 310                 315                 320

Val Ile Ile Ile Ile Leu Cys Val Pro Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Gly Asp His Arg Asp Ala Ala Gln Leu Gly Phe Gln
        355                 360                 365

Pro Leu Met Ser Ala Thr Gly Ser Thr Gly Ser Thr Glu Gly Ala
        370                 375                 380

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
agagtatatt tggaacaagg ggtca                                               25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
```

-continued

```
cccaggacat cttctgccca ctgt                                          24
```

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7

```
ggggccatgg ggctggg                                                  17
```

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8

```
atctgagatg tcggtcc                                                  17
```

<210> SEQ ID NO 9
<211> LENGTH: 1318
<212> TYPE: DNA
<213> ORGANISM: Homo sapiens
<220> FEATURE:
<221> NAME/KEY: CDS
<222> LOCATION: (545)..(1195)

<400> SEQUENCE: 9

```
cggcacgagg agaataaaaa acatttgcca agacctcatg cccttttagt aaacgaatgt    60
ttactgccac ctccagagaa gctcactgct gaggtcctag gaatcatttg cattgtcctg   120
atggccactg tgttaaaaac aatagttctt attccttgta ttggagtact ggagcagaac   180
agtttttccc tgaatagaag aatgcagaaa gcacgtcatt gtggccattg tcctgaggag   240
tggattacat attccaacag ttgttattac attggtaagg aaagaaaact tgggaagaaa   300
gagtttgctg gcctgtgctt cgaagaactc tgatctgctt tctatagata atgaggaaga   360
aatgctactg gggataaagg aaggagaaat aagtcaccta aaatttgagc acctgctaat   420
aggtatgtgt ggggacttcc cagttggctg taagttgcca tttgaactaa cgaaatagg    480 aatcctttgt gcattgaaga ctttagattc ctctctgcgg tagacgtgca cttataagta   540 tttg atg ggg tgg att cgt ggt cgg agg tct cga cac agc tgg gag atg    589
     Met Gly Trp Ile Arg Gly Arg Arg Ser Arg His Ser Trp Glu Met
     1               5                  10                  15 agt gaa ttt cat aat tat aac ttg gat ctg aag aag agt gat ttt tca    637
Ser Glu Phe His Asn Tyr Asn Leu Asp Leu Lys Lys Ser Asp Phe Ser
            20                  25                  30 aca cga tgg caa aag caa aga tgt cca gta gtc aaa agc aaa tgt aga    685
Thr Arg Trp Gln Lys Gln Arg Cys Pro Val Val Lys Ser Lys Cys Arg
        35                  40                  45 gaa aat gca tct cca ttt ttt ttc tgc tgc ttc atc gct gta gcc atg    733
Glu Asn Ala Ser Pro Phe Phe Phe Cys Cys Phe Ile Ala Val Ala Met
    50                  55                  60 gga atc cgt ttc att att atg gta gca ata tgg agt gct gta ttc cta    781
Gly Ile Arg Phe Ile Ile Met Val Ala Ile Trp Ser Ala Val Phe Leu
65                  70                  75 aac tca tta ttc aac caa gaa gtt caa att ccc ttg acc gaa agt tac    829
Asn Ser Leu Phe Asn Gln Glu Val Gln Ile Pro Leu Thr Glu Ser Tyr
```

```
                80                  85                  90                  95
tgt ggc cca tgt cct aaa aac tgg ata tgt tac aaa aat aac tgc tac          877
Cys Gly Pro Cys Pro Lys Asn Trp Ile Cys Tyr Lys Asn Asn Cys Tyr
                100                 105                 110 caa ttt ttt gat gag agt aaa aac tgg tat gag agc cag gct tct tgt          925
Gln Phe Phe Asp Glu Ser Lys Asn Trp Tyr Glu Ser Gln Ala Ser Cys
            115                 120                 125 atg tct caa aat gcc agc ctt ctg aaa gta tac agc aaa gag gac cag          973
Met Ser Gln Asn Ala Ser Leu Leu Lys Val Tyr Ser Lys Glu Asp Gln
        130                 135                 140 gat tta ctt aaa ctg gtg aag tca tat cat tgg atg gga cta gta cac         1021
Asp Leu Leu Lys Leu Val Lys Ser Tyr His Trp Met Gly Leu Val His
    145                 150                 155 att cca aca aat gga tct tgg cag tgg gaa gat ggc tcc att ctc tca         1069
Ile Pro Thr Asn Gly Ser Trp Gln Trp Glu Asp Gly Ser Ile Leu Ser
160                 165                 170                 175 ccc aac cta cta aca ata att gaa atg cag aag gga gac tgt gca ctc         1117
Pro Asn Leu Leu Thr Ile Ile Glu Met Gln Lys Gly Asp Cys Ala Leu
                180                 185                 190 tat gcc tcg agc ttt aaa ggc tat ata gaa aac tgt tca act cca aat         1165
Tyr Ala Ser Ser Phe Lys Gly Tyr Ile Glu Asn Cys Ser Thr Pro Asn
            195                 200                 205 aca tac atc tgc atg caa agg act gtg taa agatgatcaa ccatctcaat          1215
Thr Tyr Ile Cys Met Gln Arg Thr Val
        210                 215 aaaagccagg aacagagaag agattacacc agcggtaaca ctgccaaccg agactaaagg       1275
aaacaaacaa aaacaggaca aaatgaccaa agactgtcag att                         1318

<210> SEQ ID NO 10
<211> LENGTH: 216
<212> TYPE: PRT
<213> ORGANISM: Homo sapiens

<400> SEQUENCE: 10

Met Gly Trp Ile Arg Gly Arg Ser Arg His Ser Trp Glu Met Ser
 1               5                  10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45

Asn Ala Ser Pro Phe Phe Cys Cys Phe Ile Ala Val Ala Met Gly
        50                  55                  60

Ile Arg Phe Ile Ile Met Val Ala Ile Trp Ser Ala Val Phe Leu Asn
65                  70                  75                  80

Ser Leu Phe Asn Gln Glu Val Gln Ile Pro Leu Thr Glu Ser Tyr Cys
                85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
    130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175
```

```
Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
    210                 215
```

SOLUBLE MIC POLYPEPTIDES AS MARKERS FOR DIAGNOSIS, PROGNOSIS AND TREATMENT OF CANCER AND AUTOIMMUNE DISEASES OR CONDITIONS

This application is a national phase application under 35 U.S.C. §371 of International Application No. PCT/US03/12299 filed Apr. 22, 2003, which claims priority to U.S. Provisional Patent Application No. 60/374,442 filed on Apr. 22, 2002, both of which applications are specifically incorporated by reference in their entirety.

This invention was made with government support grant number R37 AI30581 awarded by the National Institutes of Health. The government has certain rights in the invention.

BACKGROUND OF THE INVENTION

1. Field of the Invention

The present invention relates generally to the field of immunology and oncology. More particularly, it concerns the diagnosis and prognosis of cancer by screening subjects for the presence of soluble and tumor cell-surface bound MIC. Further, it concerns the treatment of cancer using MIC as a cancer detection marker.

2. Description of Related Art

Cancer is the second leading cause of death in the United States producing 38,500 deaths in year of 2000. Half of all men and one-third of all women in the United States will develop cancer during their lifetimes. Today, millions of people are living with cancer or have had cancer.

Despite many therapeutic advances, early detection of malignancy has great potential as a means of affecting outcome and survival of cancer patients. Very often, the disease is too far advanced and therapeutic options are limited. Screening procedures such as Papanicolou smears for squamous cell carcinoma of the cervix are an important way of screening for cancer. The development of additional methods with similar potential for early detection of other malignancies would be of considerable aid to clinical oncologists.

Investigators have identified several substances that are produced by tumor cells for use as diagnostic markers of cancer. These include the germ cell markers human choriogonadotropin and alpha-fetoprotein, which are very specific markers, and less sensitive and specific markers such as carcinoembryonic antigen (CEA), CA-12.5, CA-19.9, CA-15.3, prostate specific antigen (PSA), and others. Recent reviews describe the use of these and other tumor markers in diagnostic and therapeutic applications (Pohl et al., 1983; Kluvins et al., 1983; Sultzeanu et al., 1985; Virji et al., 1988; and Sikorska et al., 1988). However, cancer still remains undetected in a large number of patients for lengths of time, during which beneficial treatment could have been administered. Even subsequent to treatment, it often is not known to what extent treatment effected eradication of cancer or tumor cells. Thus, additional markers are needed, as are assays based on those markers.

There is a continued need for sensitive diagnostic and prognostic methods of detecting cancer in samples that may or may not contain cancer cells and to assess the level of cancer in patients before treatment and/or after treatment.

Similarly, autimmune diseases is an area in which there exists a continued need for diagnostic, prognostic, and therapeutic methods and compositions.

Autoimmune diseases are believed to afflict approximately 14 to 22 million Americans, roughly five to eight percent of the population. They are also among the ten leading causes of death in women in every age group up until age 64. Rheumatoid arthritis (RA) alone numbers approximately 2.1 million cases in the United States, including 30,000 to 50,000 cases involving children. Treatment and diagnostics for RA, as with many other autoimmune diseases, are limited, and alternatives are needed.

SUMMARY OF THE INVENTION

The present invention concerns the observation that the level of NKG2D on CD8 T cells is systemically decreased in subjects with tumors that express MIC proteins and the further observation that MIC, previously known to be expressed on the surface of tumor cells ("bound MIC" or "cell surface MIC" or "tumor cell bound MIC") as cell membrane-anchored polypeptides, are shed from tumor cells and distributed into the circulation ("soluble MIC" or. "shed MIC"). Thus, the present invention includes methods and compositions for detecting, diagnosing, for obtaining a prognosis, staging and monitoring cancer in a patient involving detecting, identifying or assaying for soluble MIC polypeptides. It may also be used for evaluating the efficacy of a cancer treatment. A subject or patient may be someone who has not been diagnosed with cancer (diagnosis, prognosis, and/or staging) or someone diagnosed with cancer (diagnosis, prognosis, monitoring, and/or staging), including someone treated for cancer (prognosis, staging, and/or monitoring). The subject or patient may also be suspected of having cancer or of being at risk for having or developing cancer. Implementations of these evaluations involve obtaining a sample from a subject. The sample may include sputum, serum, blood, plasma, spinal fluid, semen, lymphatic fluid, urine, stool, pleural effusion, ascites, a tissue sample, tissue biopsy, cell swab, or a combination thereof. In other embodiments of the invention, a sample may include cells that are from lung, skin, muscle, liver, renal, colon, prostate, breast, brain, bladder, small intestine, large intestine, cervix, stomach, pancreas, testes, ovaries, bone, marrow, or spine. Cells may or may not be tumor cells, though in particular embodiments of the invention, tumor cells are not included in the sample because these embodiments involve assaying for soluble, as opposed to cell bound, MIC. A patient may be identified as suspected of having cancer or being at risk for having or developing cancer based on the results of a patient interview, the results of a screen or assay for factors related to or directly indicating cancer or precancerous cells/tissue. The patient interview may yield information that the person exhibits symptoms or other signs of cancer or that the patient has a familial or environmental risk for cancer. Once methods of the invention are performed involving soluble MIC polypeptides, follow-up tests may be performed to investigate further the possibility of cancer or the possibility of developing cancer.

In some embodiments of the invention, it is contemplated that the level of soluble MIC polypeptide in the sample identifies the patient either as having or at risk of having cancer or an autoimmune disease. That level may be compared to the levels observed in subjects who do not have cancer or an autoimmune disease (non-disease subjects), and found to be relatively higher than the levels in the patients who do not have cancer or an autoimmune disease. It is contemplated that in some cases a background level of soluble MIC polypeptide is in a sample and defined to be a level found in non-disease subjects. However, it is also contemplated that the presence of any soluble MIC polypeptide is indicative of cancer or an autoimmune disease.

Furthermore, methods of the invention apply to, but are not limited to, the following cancers: brain cancer, lymphatic cancer, liver cancer, stomach cancer, testicular cancer, cervical cancer, ovarian cancer, leukemia, melanoma, head and neck cancer, esophageal cancer, colon cancer, breast cancer, lung cancer, prostate cancer, and renal cancer. It is specifically contemplated for use with cancer involving all types of epithelial tumors including, but not limited to, lung, breast, gastric, colon, ovarian, renal cell and prostate carcinomas and melanoma. Diagnosis aspects of the invention concern methods for detecting cancer by detecting a soluble MIC polypeptide in a sample. In some embodiments of the invention, a sample is first obtained from a subject, who may be suspected of having cancer or pre-cancer. The MIC polypeptide may be MICA, MICB, or both.

In some embodiments of the invention, identification of a soluble MIC polypeptide involves use of at least one MIC polypeptide binding agent. The agent may be specific to either MICA or MICB, or it may recognize both. Furthermore, it is contemplated that a MIC polypeptide binding agent may be specific to soluble MIC or to bound MIC or bind to both. For example, antibodies of the invention may bind an epitope of MIC that is not available when MIC is bound to a cell. Alternatively, different conformations may serve the basis for binding agents capable of distinguishing between soluble and bound MIC. In some embodiments of the invention, the MIC polypeptide binding agent is a polypeptide.

The polypeptide is, in additional embodiments, an antibody. In further embodiments, the antibody is a monoclonal antibody, such as 2C10, 6D4, 6G6, or 3H5, or a combination thereof. Of these, 2C10 and 3H5 are specific for the membrane distal α1α2 domains of MICA and are not cross-reactive with MICB. The antibodies 6D4 and 6G6 are specific for both MICA and MICB and recognize epitopes in the α1α2 and α3 domains of the polypeptides, respectively (Groh et al., 1996, 1998). The antibody can be bi-specific, recognizing two different epitopes. The antibody, in some embodiments, immunologically binds to more than one epitope from the same soluble MIC polypeptide. Alternatively, it may bind at least one epitope in a MICA polypeptide and at least one different epitope in a MICB polypeptide.

A MIC polypeptide binding agent that is a polypeptide may also include all or part of NKG2D, which is a receptor for MIC polypeptides. The sequence of NKG2D (SEQ ID NO: 9; SEQ ID NO: 10) can be found at GenBank accession number AF461811 (Houchins et al., 1991).

In some embodiments of the invention, the MIC binding agent is labeled. In further embodiments, the label is radioactive, fluorescent, chemilluminescent, an enzyme, or a ligand. It is also specifically contemplated that a binding agent is unlabeled, but may be used in conjunction with a detection agent that is labeled. A detection agent is a compound that allows for the detection or isolation of itself so as to allow detection of another compound that binds, directly or indirectly. An indirect binding refers to binding among compounds that do not bind each other directly but associate or are in a complex with each other because they bind the same compounds or compounds that bind each other.

Other embodiments of the invention involve a second MIC polypeptide binding agent in addition to a first MIC polypeptide binding agent. The second binding agent may be any of the entities discussed above with respect to the first binding agent, such as an antibody. It is contemplated that a second antibody may bind to the same of different epitopes as the first antibody. It is also contemplated that the second antibody may bind the first antibody or another epitope than the one recognized by the first antibody. In cases in which two different epitopes are recognized by a first and second MIC polypeptide binding agent, in some embodiments at least one epitope is from MICA and the other epitope is from MICB. As discussed earlier, binding agents may be labeled or unlabeled. Any MIC polypeptide binding agent used in methods of the invention may be recognized using at least one detection agent. A detection agent may be an antibody that binds to a MIC polypeptide binding agent, such as an antibody. The detection agent antibody, in some embodiments, binds to the Fc-region of a binding agent antibody. In further embodiments, the detection agent is biotinylated, which is incubated, in additional embodiments, with a second detection agent comprising streptavidin and a label. It is contemplated that the label may be radioactive, fluorescent, chemilluminescent, an enzyme, or a ligand. In some cases, the label is an enzyme, such as horseradish peroxidase.

The present invention also covers methods involving using an ELISA assay to identify a soluble MIC polypeptide. In some embodiments, the ELISA assay is a sandwich assay. In a sandwich assay, more than one antibody will be employed.

Additional embodiments of the methods of the invention involve NKG2D as a binding agent and a second binding agent as an antibody that immunologically binds NKG2D. Alternatively, in other embodiments of the invention, a soluble MIC polypeptide is detected by assaying for NKG2D, which has been shown to have reduced expression as a result of soluble MIC polypeptide compared to the level of NKG2D in the absence of the MIC polypeptide. Thus, a decreased level of NKG2D is indicative of the presence of soluble MIC polypeptide. The level of NKG2D can be assayed using an NKG2D binding agent, which is an agent that specifically binds NKG2D. It is contemplated that an NKG2D binding agent is an antibody, while in other embodiments, the NKG2D binding agent is a MIC polypeptide. In still further embodiments, NKG2D is assayed by assaying the amount of an NKG2D transcript, which can be accomplished by a number of procedures, some of which involve a nucleic acid complementary to at least a portion of the sequence of a NKG2D transcript or a cDNA made from the transcript. The complementary nucleic acid can be used to assay for NKG2D transcript through nucleic acid amplification, such as the polymerase chain reaction or a combined amplification/ELISA procedure.

Other methods of the invention further include assaying a sample for a cell-bound MIC polypeptide in addition to a soluble polypeptide. The second assay may be performed on the same sample as the identification of a soluble MIC polypeptide or it may be performed on a different sample. It is contemplated that a sample may or may not include cells.

As discussed above, methods of the invention can be employed to detect cancer. Such methods may implement diagnostic, prognostic, staging, or monitoring functions. In some embodiments of the invention, identification of soluble MIC polypeptide is indicative of the presence of a tumor cell. In other embodiments, identification of a soluble MIC polypeptide is indicative of negative cancer prognosis, particularly if the level of soluble MIC polypeptide is high compared to patients known to have fewer cancer or tumor cells. In a patient whose cancer was diagnosed and treated, an inability to identify the soluble MIC polypeptide in the sample indicates the patient no longer has cancer or that the patient has a positive prognosis. A positive prognosis is one in which the patient's cancer is considered to have been eliminated, reduced, retarded, or altered in any way that improves the condition of the patient. Alternatively, the presence of a soluble MIC polypeptide indicates a patient, in some embodiments, continues to have cancer or tumor cells. A negative prognosis is the opposite of a positive prognosis or it is the absence of a positive prognosis.

Other specific embodiments of the invention include methods for detecting cancer, cancer cells, or tumor cells in a subject by at least the following steps: (a) obtaining a sample from the subject; and, (b) detecting a soluble MIC polypeptide in the sample involving (i) contacting a sample from the subject with a first antibody attached to a solid support, wherein the first antibody binds to a soluble MIC polypeptide in the sample; and (ii) incubating the sample with a second antibody, wherein the second antibody binds to the soluble MIC polypeptide and is detected by a variety of methods.

In still further specific embodiments, the present invention concerns methods for treating cancer comprising: (a) detecting cancer in a subject by obtaining a sample from the subject and detecting a soluble MIC polypeptide in the sample; and, (b) administering to the subject chemotherapy, radiation therapy, gene therapy, or hormone therapy. In some embodiments the subject is provided with chemotherapy and/or radiotherapy.

The present invention also includes kits for detecting cancer comprising, in a suitable container means, a soluble MIC polypeptide binding agent (a compound that specifically binds soluble MIC polypeptide) or a soluble MIC-specific binding agent (a compound that binds only soluble polypeptide and not cell bound MIC). In further embodiments, the binding agent is labeled or a detection agent is included in the kit. It is contemplated that the kit may include a MIC polypeptide binding agent attached to a non-reacting solid support, such as a tissue culture dish or a plate with multiple wells. It is further contemplated that such a kit includes a detectable agent in certain embodiments of the invention.

The word "identify," when used in the context of the present invention may mean determination of the identity of a substance when present, but also includes the detection of the mere presence of the substance and may include the measurement of the abundance of the substance, either independently or relative to another substance or relative to a phenomenon's occurrence or magnitude, including, for example, phenotypic or medical conditions.

The present invention also concerns methods and compositions related to autoimmune diseases or conditions. As discussed herein, the inventors have found that soluble MIC polypeptide is present in patients with the autoimmune condition rheumatoid arthritis. Therefore, the present invention involves methods and compositions for the prognosis, diagnosis, and/or treatment of patients who have an autoimmune disease or condition, who are suspected of having an autoimmune disease or condition, or who are at risk of having or developing an autoimmune disease or condition. Also, because the inventors have observed that the interaction between MIC polypeptides and NKG2D on synovial fibroblasts plays a role in autoimmune diseases and/or conditions, methods of identifying candidate therapeutic agents for those diseases and conditions, as well as the candidate therapeutic agents are considered part of the invention.

In some embodiments of the invention, there are methods for diagnosing or prognosing an autoimmune disease or condition in a patient or subject comprising (a) identifying a patient suspected of having an autoimmune disease or condition; and, (b) assaying for a soluble MIC polypeptide in a sample from the patient, wherein identification of a soluble MIC polypeptide in the sample indicates an autoimmune disease or condition. Identifying a patient suspected of having an autoimmune condition or disease can involve conducting a patient interview, taking a patient history or family history, assaying for anti-nuclear antibodies, taking x-rays, doing blood work on the patient (taking blood and performing tests on the blood), conducting a physical exam, assaying for Rheumatoid factor or other factors that may indicate an autoimmune disease or condition, or administering a drug or other therapeutics (or counseling about performing certain exercises or avoiding certain activities) used for the treatment of that autoimmune disease and monitoring efficacy. Embodiments for assaying for a soluble MIC polypeptide are discussed above with respect to cancer, and are specifically contemplated for use with respect to autoimmune diseases and conditions.

In still further embodiments of the invention, a sample is obtained from a patient or subject for evaluation. The sample can include sputum, serum, blood, plasma, spinal fluid, semen, lymphatic fluid, urine, ascites, pleural effusion, or stool. Furthermore, the sample, in some embodiments, is obtained from a region exhibiting one or more signs of inflammation.

It is contemplated that in some embodiments of the invention, a subject is also administered an autoimmune disease therapeutic agent, which refers to an agent used in the treatment of an autoimmune disease. Such treatments include, but are not limited to, anti-inflammatory agents and/or immune response suppressors, surgery, physical and/or occupational therapy. In some embodiments, the patient is given NSAIDs, aspirin, analgesics, glucocorticoids, methotrexate, leflunomide, D-Penicillamine, sulfasalazine, gold therapy, minocycline, azathioprine, hydroxychloroquine (and other antimalarials), cyclosporine, biologic agents, or Prosorba. In specific embodiments, the patient is given ENBREL™, which is a recombinant tumor necrosis factor $\alpha$ receptor; this receptor acts to neutralize TNF-$\alpha$, which induces expression of NKG2D on CD4 cells. In additional embodiments, an agent that neutralizes of inhibits interleukin-15 (IL-15) can be administered to the patient alone or in combination with any other therapeutic agent.

Methods of screening for candidate therapeutic agents for an autoimmune disease or condition are also included as part of the invention. In some embodiments, a method of screening for candidate therapeutic agents for an autoimmune disease comprises: (a) contacting a MIC polypeptide with an NKG2D receptor polypeptide in the (i) presence and (ii) absence of a candidate substance; (b). assaying for binding between the MIC polypeptide and the NKG2D receptor in (i) and (ii), wherein a reduction of binding in (i) compared to (ii) is indicative of a candidate therapeutic agent for an autoimmune disease. Alternatively, the method may involve assaying for the ability of the candidate substance to bind a MIC polypeptide and/or the NKG2D receptor. An assay may be done in the presence and/or absence of the candidate substance to determine whether the candidate substance is the agent giving rise to an observed effect.

In some screening methods, the candidate substance is a small molecule, PNA, peptide mimetic, or proteinaceous composition. It is contemplated that the proteinaceous composition could be a protein, polypeptide, or peptide. In some cases, it may be all or part of antibody that specifically binds to NKG2D or a MIC polypeptide. Alternatively, it may be a compound that mimics and effectively competes with the MIC polypeptide (ligand) to bind NKG2D (receptor), or vice versa.

In some cases, a candidate therapeutic agent has been identified and further testing may be required. In some embodiments the further testing is to evaluate a candidate therapeutic agent (or an agent that has been confirmed to be therapeutic) for quality control and/or safety concerns. In some embodiments, methods of the invention include a method of assaying a therapeutic agent (or candidate therapeutic agent) for efficacy against an autoimmune disease comprising: (a) contacting a MIC polypeptide with an NKG2D receptor polypeptide in the (i) presence and (ii) absence of the candidate substance, wherein the candidate substance is substantially pure; (b) assaying for binding between the MIC polypeptide and the NKG2D receptor in (i) and (ii), wherein a reduction of binding in (i) compared to (ii) indicates the candidate substance has the ability to reduce binding between the MIC polypeptide and the NKG2D receptor. The term "substantially pure" refers to a compound that is at least about 80%, 85%, 90%, 95% or more pure with respect to contaminating substances, i.e., substances from which the compound is trying to be separated or isolated. The candidate substance may have been produced on a large-scale.

The present invention also concerns compositions for carrying out methods of the invention. Thus, in some embodiments the invention concerns kits for diagnosing or prognosing cancer or an autoimmune disease in a patient comprising, in suitable container means: (a) an agent that specifically recognizes all or part of a MIC polypeptide or a nucleic acid encoding a MIC polypeptide; and, (b) a positive control that can be used to determine whether the agent is capable of specifically recognizing all or part of a MIC polypeptide or a nucleic acid encoding a MIC polypeptide. The kit may also include other reagents that allow visualization or other detection of the MIC polypeptide, such as reagents for colorimetric or enzymatic assays.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

I. The Present Invention

Figure 1:
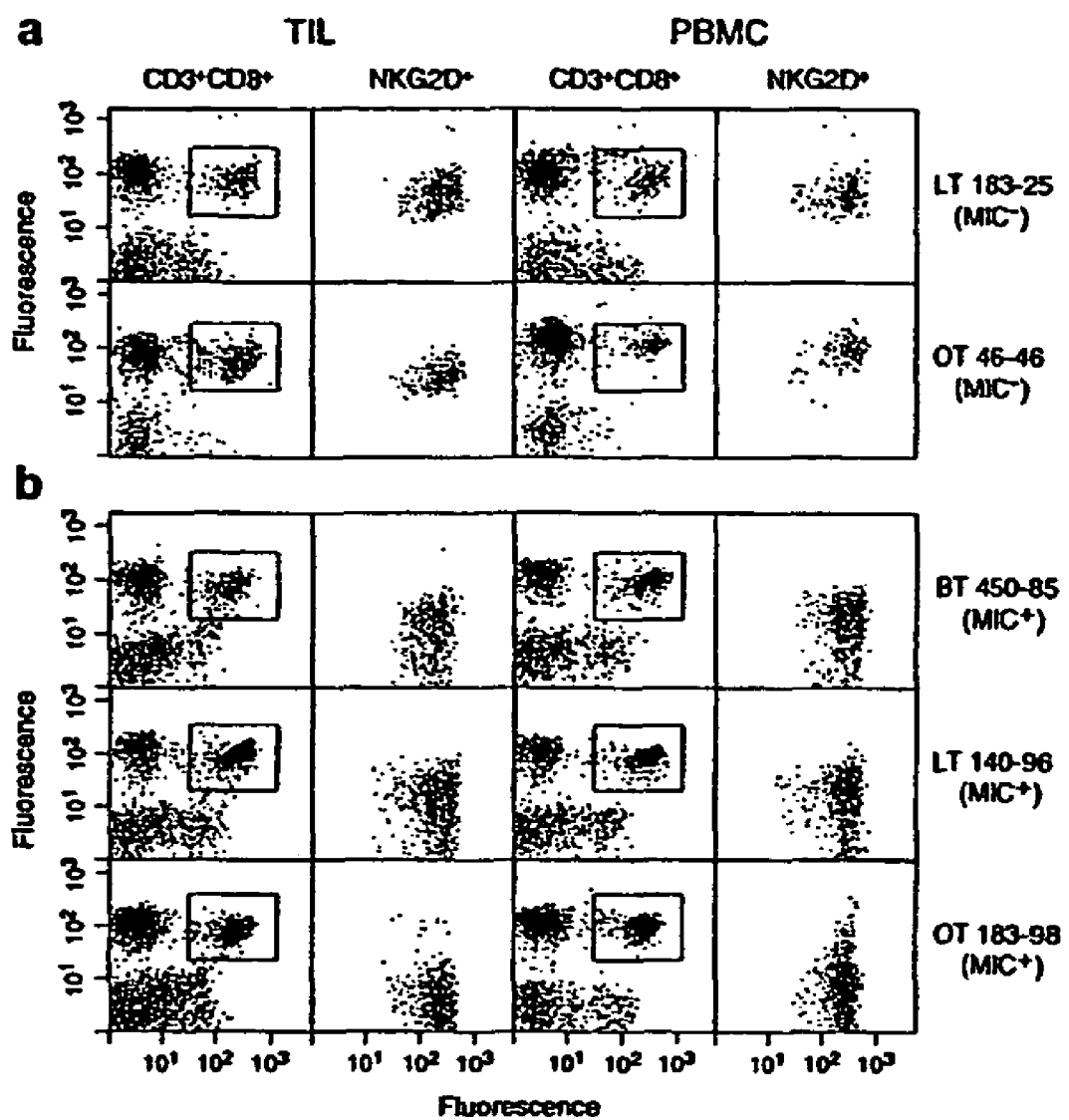
FIG. 1A. NKG2D expression is normal in subjects with tumors that are negative for MIC as determined by flow cytometry stainings of freshly isolated tumor cell suspensions. Codes at right identify tumor samples. LT, lung tumor; OT, ovarian tumor; BT, breast tumor. The results shown are representative of 27 tumors tested FIG. 1B. Systemic downmodulation of NKG2D on CD3/CD8 T cells derived from tumor infiltrating lymphocytes (TIL) and peripheral blood mononuclear cells (PBMC) from patients with tumors that were positive for MIC by antibody staining and flow cytometry of freshly prepared tumor cell suspensions. (bottom 3 panels). Codes at right identify tumor samples. LT, lung tumor; OT, ovarian tumor; BT, breast tumor. The results shown are representative of 27 tumors tested.

MICA and MICB are proteins that have been shown to be frequently expressed on epithelial tumor cells including lung, breast, gastric, colon, renal cell, ovarian and prostate carcinomas and melanoma (Groh et al., 1999). MIC are thus the most widely distributed tumor-associated proteins known.

MIC molecules interact with NKG2D, which is an activating immunoreceptor on the surface of CD8 T-cells and natural killer (NK) cells (Bauer et al., 1999). When NKG2D binds to its MIC ligands on tumor cells or virus-infected cells, it potently augments antigen-specific T cell responses. Thus, the regulation of NKG2D has important physiological implications since its functional capacities are impaired under conditions of diminished expression.

Engagement of NKG2D by MIC potently stimulates effector T cell responses directed against cells expressing tumor- or virus-specific antigens (Groh et al., 2001). These responses include cytotoxicity, cytokine production and T cell proliferation. Because MIC proteins are not expressed on healthy cells and tissues, except for intestinal epithelium (Groh et al., 1996), and because they are induced by cellular stress (Groh et al., 1998), MIC and the NKG2D receptor represent an emergency defense system that has the capacity to boost immune responses against tumors and pathogen-infected cells.

However, as with other activating immunoreceptors, NKG2D is downmodulated after binding of its MIC ligands, presumably to prevent excessive T cell activation. It has been shown that diminished expression of NKG2D abrogates T cell responsiveness to MIC expressing targets such as tumor cells. Tumors frequently counteract immunesurveillance by mechanisms that are still poorly understood. The inventors have found that significant proportions of T cells in the circulation of many cancer patients have diminished levels of NKG2D and are unresponsive against tumor target cells. Peripheral blood serum samples from these patients contain substantial amounts of tumor-derived soluble MIC proteins with the capacity to downregulate NKG2D. Thus, diminished expression of NKG2D and detectable soluble MIC in serum samples are indicators for the presence of cancer and can be used for the diagnosis and prognosis of cancer.

The inventors show that diminished expression of NKG2D occurs in tumor patients as a result of its interaction with soluble MIC that is shed from tumor cells. Thus, soluble MIC can be used as an important detection marker to identify the presence of cancer. It may be used in situations where a subject is not suspected of having cancer, but the presence of soluble MIC in a blood serum or other sample is indicative of the presence of cancer. It may also be used as a tool for staging tumors wherein a person undergoing treatment is monitored to analyze the extent to which the patient further needs to be treated to remove completely any tumor from the body. Further, the presence of soluble MIC may be useful in a long-term treatment strategy where the patient is completely rid of tumor but needs to be periodically monitored for the recurrence of tumor. If the patient shows signs of cancer or tumor cells, cancer therapy, such as chemotherapy or radiotherapy, may be implemented.

The present invention, therefore, provides methods and compositions of detection, assay, prognosis, monitoring, and treatment of cancer in a patient involving assays for soluble MIC polypeptide or assaying both soluble and tumor cell-surface MIC polypeptides in a patient.

Furthermore, the inventors have shown that soluble MIC polypeptides can be detected in patients with an autoimmune disease, and that the MIC polypeptides contributes to the disease state. Therefore, the present invention provides methods and compositions of detection, assay, prognosis, monitoring, and treatment of autoimmune diseases and conditions in a patient involving assays for soluble MIC polypeptide, as well as screening methods to identify compounds that disrupt or interfere with the ability of MIC polypeptides and their NKG2D receptors to interact.

II. Proteinaceous Compositions

A. NKG2D Receptors

NKG2D, a homodimeric C-type lectin-like receptor, is a unique stimulatory molecule that is found on natural killer (NK) cells CD8 alpha beta T cells and gamma delta T cells. It is associated with an adaptor protein, DAP10, through oppositely charged amino acid residues in their transmembrane domains. DAP10 signals similarly to the CD28 co-stimulatory receptor by activation of phosphatidylinositol 3-kinase (PI3K) upon phosphorylation of a YxxM motif in its cytoplasmic domain. The deglycosylated NKG2D polypeptide chain is of 28 kilodalton (kD). It is encoded by a gene in the NK complex (NKC) on human chromosome 12. Despite its name, NKG2D shares no significant sequence homology with the NKG2A and NKG2C/H receptors that associate with CD94. NKG2D homodimers form stable complexes with monomeric MICA in solution, indicating that no other components are required to facilitate this interaction. Soluble NKG2D also binds to cell surface MICB, which has structural and functional properties similar to those of MICA (Steinle et al., 2001).

MICA and MICB are distant relatives of MHC class I molecules but have no function in antigen presentation. Instead, they function as signals of cellular distress. These proteins have a highly restricted tissue distribution in intestinal epithelium and are frequently expressed in epithelial tumors (Groh et al., 1996, 1999). Epithelial tumors are those that arise from surface or lining tissues. Epithelial cells cover surfaces and line internal passage ways. As such, epithelial tissue is found in 3 major places: outer surfaces of the body; surfaces of organs and internal surface lining of tubules, vessels and hollow organs. Most glands are composed primarily of epithelial cells. Therefore, epithelial tumors may be found on any surface or lining of the body that fits the above description.

The inventors discovered that NKG2D functions as a receptor for MICA and MICB using biochemical and genetic methods (Bauer et al. 1999). Prior to this finding, the function of NKG2D was unknown. The inventors determined that NKG2D has a very broad distribution on lymphocyte subsets, being expressed on most NK cells, CD8 alpha beta T cells and gamma delta T cells. Functional experiments showed that engagement of NKG2D activates cytolytic responses of gamma delta T cells and NK cells against transfectants and epithelial tumor cells expressing MIC (Groh et al., 1999; Bauer et al., 1999). These results define an activating immunoreceptor-MHC ligand interaction that may promote antitumor NK and T cell responses. Furthermore, the inventors showed that interactions of MIC with NKG2D potently augment cytolytic responses of antigen-specific CD8 alpha beta T cell responses and co-stimulate cytokine production and T cell proliferation (Groh et al., 2001).

Rheumatoid arthritis (RA) is an often disabling chronic autoimmune and inflammatory joint disease. Its severity correlates with large numbers of CD4+CD28− T cells, which are scarce in healthy individuals. For poorly defined reasons, these T cells are autoreactive, implying that they may contribute to disease manifestations.

Maintaining effective immunesurveillance without provoking autoimmune reactions requires the precise titration of effector T-cell responses. This fine-tuning may involve the integration of negative or positive signals transduced by inhibitory or activating isoforms of the killer cell immunoglobulin (Ig)-like receptors (KIR), which interact with major histocompatibility complex (MHC) class I HLA-A, -B, or -C alleles, and the inhibitory CD94-NKG2A and activating CD94-NKG2C heterodimers, which bind HLA-E. Some of these receptors have the capacity to modulate thresholds of T-cell antigen receptor (TCR)-dependent T-cell activation (Ravetch et al., 2000; Lanier, 2001). For example, CD8 T cells express inhibitory CD94-NKG2A receptors after persistent antigen-driven stimulation, which downmodulate effector responses in chronic infections and malignancies but may safeguard against autoimmune reactions (Mingari et al., 1996; Speiser et al., 1999; Moser et al., 2002). By contrast, the role of activating KIR isoforms and CD94-NKG2C in T-cell modulation is less clear, mainly because they are usually coexpressed with their inhibitory counterparts, which have higher ligand affinities and thus convey dominant negative signals (Ravetch et al., 2000; Lanier, 20013). However, in the rare absence of inhibitory receptors, the activating isoforms may augment T-cell effector functions and contribute to autoimmune pathology (Namekawa et al., 2000; Yen et al., 2001). This is supported by the association of disease severity in rheumatoid arthritis (RA) with expression of the activating KIR2DS2 receptor by autoreactive CD4+CD28− T cells in individuals with proper HLA-C ligand alleles.

An activating receptor lacking an apparent antagonist is NKG2D, which interacts with the MHC class I-related MICA and MICB glycoproteins among other ligands (Bauer et al., 1999). These have no role in antigen presentation, have a restricted tissue distribution in intestinal epithelium, and can be stress-induced in permissive types of cells by viral and bacterial infections, malignant transformation and proliferation (Groh et al., 1996; Groh et al., 1998; Groh et al., 1998; Das et al., 2001; Groh et al. 2001; Tieng et al., 2002). NKG2D is a C-type lectin-like activating receptor that signals through the associated DAP10 adaptor protein similar to CD28 (Wu et al., 1999). It is expressed on most NK cells, CD8 T cells and γδ T cells, but not on CD4 T cells (Bauer et al., 1999). Ligand engagement of NKG2D activates NK cells and potently costimulates effector T cells (Bauer et al., 1999; Das et al., 2001; Groh et al. 2001). However, the expression of NKG2D is controlled by ligand-induced downmodulation, which is transient and rapidly reversed by interleukin-15 (Groh et al., 2002).

Because ligand binding unconditionally triggers lymphocyte activation or costimulation by NKG2D, its dysregulation, and anomalous expression of MIC in local tissue environments could promote autoreactive T-cell stimulation. In the present report, we explored this possibility in the context of the pathology of RA, which involves lymphocyte infiltrates, inflammatory mediators, and synovial hyperplasia due to proliferation of fibroblast-like synoviocytes and macrophages (Feldmann, 1996; Ivashkiv, 1996). Prognosis of joint erosions and disease severity in RA correlate with high frequencies of clonally expanded CD4+CD28− T cells, which are rare in healthy individuals but occur in other autoimmune disorders (Miller et al., 1996; Chapman et al., 1996; Schmidt et al., 1996; Martens et al., 1997; Snyder et al., 2002). Upon stimulation with autologous peripheral blood-derived adherent cells and endothelial cells in vitro, these T cells can be cytotoxic and secrete large amounts of interferon-γ (IFN-γ) and tumor necrosis factor-α (TNF-α) (Schmidt et al., 1996; Snyder et al., 2002; Park et al., 1997). Although this aggregate evidence is insufficient to directly implicate CD4+CD28− T cells in autoimmunity in RA, their often massive expansion and unusual properties suggest some involvement in this disease.

B. MICA and MICB Proteins

The present invention contemplates the use of MIC proteins as an important marker for screening samples from subjects for prognostic and diagnostic purposes and for treatment of cancer. The methods by which such screening takes place are well known in the art and described further below.

In one embodiment of the invention, the present application thus describes the importance of soluble MIC in the detection of cancer wherein the soluble MICA and MICB shed by tumor cells provides a marker for diagnostic screening methods for cancer in samples such as sputum, tears, blood, plasma, spinal fluid, semen, lymphatic fluid, urine, stool, pleural effusion and ascites. As mentioned earlier in the specification, the combination of both soluble and tumor cell-surface bound MIC may also be employed to detect cancer. Thus, one of the embodiments of the invention envisions detection and quantitation assays.

MICA and MICB proteins (SEQ ID NO: 2 and SEQ ID NO: 4, respectively) are MHC class I related Chains A and B. They are closely related and are encoded by genes 40 and 110 kilobases (kb) centromeric of HLA-B, respectively (Bahram et al., 1994). Sequences directly homologous to MIC are conserved in most mammals except rodents, and thus probably originated at an early stage in mammalian evolution. The translation product of MICA is only distantly similar to mammalian MHC class I chains, but it shares the same domain organization and predictably a similar tertiary structure. An average of 25% of the MICA amino acids in the extracellular $\alpha 1$, $\alpha 2$, and $\alpha 3$ domains match residues in diverse human and mouse, or in any other mammalian MHC class I sequences (Bahram et al., 1994). A further characteristic of MICA is the complete absence of all of the residues implicated in the binding of CD8 and the presence of eight N-linked glycosylation sites in the $\alpha 1$-$\alpha 3$ domain sequences. Moreover, transcription of MICA is restricted to various epithelial cell lines and is not regulated by γ-interferon. MICB mRNA is present in the same cell lines, albeit at very low levels. In epithelial cell lines, transcription of both MICA and MICB can be induced by heat shock in a manner similar to heat shock protein 70 (hsp70), presumably owing to the presence of putative heat shock elements (HSE) in the 5' flanking regions of both MICA and MICB (Groh et al., 1996, 1998). Because of this property, MICA and MICB are cell stress response genes.

The inventors have reported the complete nucleotide sequence of the MICA gene comprising 11,722 basepairs (bp) of DNA 40 kilobases (kb) centromeric of HLA-B. The MICA cDNA is referred to as SEQ ID NO: 1. The sequence was obtained from single-stranded (M13) and double-stranded (pUC19) templates of mapped or randomly shot-gun subcloned DNA fragments that were derived from the cosmid M32A (Spies et al., 1989). The first exon encoding the leader peptide is followed by an intron of 6840 bp, which is unusually large for a class I gene. The remainder of the MICA gene shows an organization quite similar to that of conventional class I genes, except for the presence of a relatively long intron following the transmembrane exon and the fusion of the cytoplasmic tail and 3' untranslated sequence in a single last exon.

The MICB gene has been mapped in cloned cosmids by DNA blot hybridizations using a MICA cDNA probe. It corresponds to mRNA of about 2.4 kb, distinct from MICA mRNA, which is 1.4 kb in size (Bahram et al., 1994). A partial 2304 base pairs (bp) MICB cDNA clone lacking the leader peptide sequence was isolated from an IMR90 human lung fibroblast library by screening with the MICA cDNA probe. The missing 5' end sequence was cloned by a 5' Rapid Amplification of cDNA ends polymerase chain reaction (RACE-PCR) procedure (5'-AMPLIFINDER™ RACE kit; Clontech, Palo Alto, Calif.) after reverse transcription (RT) of poly(A)+ HeLa cell mRNA in the presence of a specific RT primer (3'-ACTGGGGAACAAGGTTTATATGAGA-5', MICB nucleotides 1653-1677; SEQ ID NO:5). Purified first-strand cDNA was ligated to a 5' anchor oligonucleotide with T4 RNA polymerase, and amplified by PCR using anchor primer and an MICB oligonucleotide (3'-TGTCACCCGTCTTCTA-CAGGACCC-5', MICB nucleotides 215-238; SEQ ID NO:6). The amplified 250 bp DNA fragment was directly cloned in pCRII (Invitrogen, San Diego, Calif.) and sequenced. A cDNA including the complete MICB coding sequence was subsequently generated by RT-PCR and cloned, using the same RT primer and PCR primers flanking the single long open reading frame (5'-(Sal I)-GGGGCC ATGGGGCTGGG-3' SEQ ID NO:7, and 3'-ATCTGAGATGTCGGTCC-(Bam HI)-5' SEQ ID NO:8). The full-length MICB cDNA sequence of 2380 bp encodes a polypeptide of 383 amino acids that begins with a probable translation initiation codon (ATG) at nucleotide position 6 (Bahram and Spies, 1996). The MICB cDNA is referred to as SEQ ID NO: 3. The stop codon is followed by a relatively long 3' untranslated region, which accounts for the size difference of the MICB and MICA mRNAs. A consensus polyadenylation signal near the 3' end of the MICB cDNA is missing; the nearest AATAAA sequence is located 772 bp upstream and an appropriately positioned alternative polyadenylation signal is not readily discernible (Wickens, 1990).

The MICB translation product is identical to the MICA chain in length and domain organization and is highly similar, with 83% matching amino acid residues. Of the total of 65 amino acid substitutions, 18 are clustered within a segment of 24 amino acids in the putative transmembrane segment of MICB, which represents the sole highly disparate portion of the aligned sequences. In the $\alpha 1$-$\alpha 3$ domains, MICB and MICA share 86% amino acid sequence similarity, with 15, 14, and 8 amino acid substitutions in the $\alpha 1$, $\alpha 2$, and $\alpha 3$ domains, respectively, which show no notable preferential distribution. Like MICA, the putative MICB chain may be heavily glycosylated, owing to the presence of five potential N-linked glycosylation sites, of which four in the α3 domain are common to both sequences. None of the three N-linked glycosylation motifs in MICA α1 and α2 are conserved in MICB, which has one such motif in the α2 domain. The highly conserved glycosylation site at amino acid position 86 in MHC class I chains is missing in MICB and MICA. Both sequences include the two pairs of cysteines in the α2 and α3 domains, which form intradomain disulfide bonds in class I chains, and several extra cysteine residues.

Common to MICB and MICA is a gap in the α1 domain, which corresponds to the peptide side chain-binding pocket B ("45" pocket) in many MHC class I chains, and an insertion of 6 amino acids at position 147 in the α2 domain (Bahram et al., 1994). Overall, MICB shows the same degree of divergence from mammalian MHC class I chains as MICA, with most of the amino acid residues that are invariant among vertebrate class I sequences being conserved (Grossberger and Parham, 1992; Bahram et al., 1994). Thus, altogether, MICB and MICA are very closely related and were probably derived by a relatively-recent gene duplication.

Additional sequences similar to MICA and MICB (MICC, MICD, and MICE) have been localized in the human MHC near the HLA-E, -A, and -F genes using yeast artificial chromosome (YAC) clones spanning the class I region (Bahram et al., 1994). By partial genomic sequencing of corresponding cosmid DNA, these three sequences were identified as truncated gene fragments. Thus, MICA and MICB are the only functional members in this family of highly diverged MHC class I genes. This is similar to the existence of numerous class I pseudogenes and gene fragments in the human MHC and mouse H2 complex (Stroynowski, 1990; Geraghty, 1993).

The inventors have studied the expression of MIC polypeptides using their specific antibodies, transfected mutant cell lines and normal epithelial tumor cell lines. The results from these and other experiments established that, contrary to MHC class I molecules, MIC are not associated with β2-microglobulin and peptides (Groh et al., 1996, 1998). Both MICA and MICB are highly glycosylated; the deglycosylated polypeptides are of 43 kilodalton (kD). The crystal structure of MICA shows rearranged domain interfaces precluding binding of β2-microglobulin and the absence of a peptide binding groove (Li et al., Immunity 10: 577-584, 1999). The interaction of MICA with NKG2D homodimers has been refined by the complex crystal structure of these molecules (Li et al., Nat. Immunol. 2: 443-451, 2001).

C. Peptides, Polypeptides, and Fragments Thereof

Proteinaceous compositions are involved in screening, prognostic and treatment methods of the invention. The present embodiment of the invention contemplates the detection of soluble MICA and MICB proteins or fragments thereof. In this application, the amino acid sequences of full-length MICA and MICB proteins are referred to as SEQ ID NO:2 and SEQ ID NO:4, respectively. Furthermore, in some embodiments of the invention, proteinaceous compositions are used to identify soluble and bound MIC polypeptides, such as MIC binding agents. Additionally, proteinaceous compounds are used as detection agents in methods of the invention or they may be a labeling moiety as part of the detection agent. It is contemplated that any teaching with respect to one particular proteinaceous composition may apply generally to other proteinaceous compositions described herein.

As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments of the invention, the proteinaceous composition may include such molecules that bear the size of at least one proteinaceous molecules that may comprise but is not limited to 1, 2, 3, 4, 5,6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 383, 385 or greater amino molecule residues, and any range derivable therein. Such lengths are applicable to all polypeptides and peptides mentioned herein, including SEQ ID NO:2 and SEQ ID NO:4. It is contemplated that MIC binding agents may specifically bind or recognize a particular region of MIC, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 383, 385 or greater contiguous amino acids of SEQ ID NO:2 or SEQ ID NO:4 or any range of numbers of contiguous amino acids derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

The term "functionally equivalent codon" is used herein to refer to codons that encode the same amino acid, such as the six codons for arginine and serine, and also refers to codons that encode biologically equivalent amino acids. Codon usage for various organisms and organelles can be found in codon usage databases, including, for example that made available by Nakamura (2002), which allows one of skill in the art to optimize codon usage for expression in various organisms using the disclosures herein. Thus, it is contemplated that codon usage may be optimized for other animals, as well as other organisms such as a prokaryote (e.g., an eubacteria, an archaea), an eukaryote (e.g., a protist, a plant, a fungi, an animal), a virus and the like, as well as organelles that contain nucleic acids, such as mitochondria, chloroplasts and the like, based on the preferred codon usage as would be known to those of ordinary skill in the art.

It will also be understood that amino acid sequences or nucleic acid sequences of MICA and MICB polypeptides, MIC polypeptide binding agents, or detection agents may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes. In some embodiments, the C-terminal or N-terminal of the MIC polypeptide may also be glycosylated.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid |
| --- | --- |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In certain embodiments, the proteinaceous composition of the MICA and MICB polypeptides comprises at least one protein, polypeptide or peptide. In further embodiments the proteinaceous composition comprises a biocompatible protein, polypeptide or peptide. As used herein, the term "biocompatible" refers to a property of being biologically compatible thus producing no significant untoward effects when applied to, or administered to, a given organism according to the methods and amounts described herein. In particular embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. For example, the Genbank and GenPept databases are available from the National Center for Biotechnology Information and are available online at the webpage for NCBI National Library of Medicine at the NIH (NCBI webpage, 2002). The coding regions for these known genes may be amplified and/or expressed using the techniques disclosed herein or as would be known to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

It is contemplated that virtually any protein, polypeptide or peptide containing component may be used in methods disclosed herein. However, it is preferred that the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

The term "full-length" refers to a MIC polypeptide that contains at least the 385 and 383 amino acids encoded by the MICA and MICB transcripts, respectively. The term "substantially full-length" in the context of MICA and MICB refers to a MIC polypeptide that contains at least 80% of the contiguous amino acids of the full-length MIC polypeptide. However, it is also contemplated that MIC polypeptides containing at least about 85%, 90%, and 95% of SEQ ID NO: 2 or SEQ ID NO: 4 are within the scope of the invention as "substantially full-length" MIC.

The term "biologically functional equivalent" is well understood in the art and is further defined in detail herein. Accordingly, a sequence that has between about 70% and about 80%; or more preferably, between about 81% and about 90%; or even more preferably, between about 91% and about 99%; of amino acids that are identical or functionally equivalent to the amino acids such as in SEQ ID NO: 2 or SEQ ID NO: 4 will be a sequence that is "essentially as set forth in SEQ ID NO: 2 or SEQ ID NO: 4 respectively," provided the biological activity of the protein, polypeptide, or peptide is maintained.

The term "functionally equivalent codon" is used herein to refer to codons that encode the same amino acid, such as the six codons for arginine and serine, and also refers to codons that encode biologically equivalent amino acids.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the MICA and MICB nucleotide. As will be mentioned later in the specification, the cDNA sequence that encodes MICA protein is referred to as SEQ ID NO:1 and the cDNA sequence that encodes MICB protein is referred to as SEQ ID NO:3.

Recombinant vectors and isolated nucleic acid segments may variously include the coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent MIC proteins, polypeptides, or peptides, as well as MIC polypeptide binding agents, and detection agents. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Recombinant changes may be introduced, for example, through the application of site-directed mutagenesis techniques as discussed herein below, e.g., to introduce improvements or alterations to the antigenicity of the protein, polypeptide or peptide, or to test mutants in order to examine MIC protein, polypeptide, or peptide activity at the molecular level.

The following is a discussion based upon changing of the amino acids of a protein, which in the present invention, may be SEQ ID NO: 2 or SEQ ID NO: 4, or a MIC polypeptide binding agent such as an antibody, to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); almandine (−0.5); histidine *−0.5); cysteine (−1.0); methionine (−1.3); valine (−1.5); leucine (-1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing compounds, that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of MIC antigen or other MIC marker antigens, but with altered and even improved characteristics. The same can be applied to MIC antibodies or any other moiety that can serve as a targeting moiety.

Sequence variants of the polypeptide, as mentioned above, can be prepared. These may, for instance, be minor sequence variants of the polypeptide that arise due to natural variation within the population or they may be homologues found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below in the following section.

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR can be used to prepare a range of cDNAs encoding peptides lacking successively longer fragments of the C-terminus of the protein. The immunoprotective activity of each of these peptides then identifies those fragments or domains of the polypeptide that are essential for this activity. Further experiments in which only a small number of amino acids are removed at each iteration then allows the location of the antigenic determinants of the polypeptide.

Another embodiment for the preparation of the polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successfil applications of the peptide mimetic concept have thus far focused on mimetics of β-turns within proteins, which are known to be highly antigenic. Likely β-turn structure within a polypeptide can be predicted by computer-based algorithms as discussed above. Once the component amino acids of the turn are determined, peptide mimetics can be constructed to achieve a similar spatial orientation of the essential elements of the amino acid side chains.

Modification and changes may be made in the structure of a gene and still obtain a functional molecule that encodes a protein or polypeptide with desirable characteristics. The following is a discussion based upon changing the amino acids of a protein to create an equivalent, or even an improved, second-generation molecule.

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 nucleotides on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In one embodiment of the invention, soluble forms of MICA or MICB are produced by recombinant expression of a truncated MICA or MICB coding regions. In another embodiment, a truncated MICA or MICB lacks the transmembrane domain and cytoplasmic tail and includes the three extracellular domains. Such truncated forms of the invention may be expressed from suitable host cells including yeast, mammalian, and insect cells using regulatory sequences, vectors and methods well established in the literature. To facilitate purification and/or identification of the truncated molecules, it may be preferable to include a sequence encoding a tag. The use of antigenic and other tags are well established and include Myc-tags, hemaglutinin tags and His tags. His tags in which the cloning sequence of interest is joined in-frame with a sequence encoding oligomeric histidines permit the purification of the resulting proteins using metal-affinity chromatography. Soluble MICA or MICB proteins produced in this manner may be used to block the function of MICA or MICB by competing with proteins that interact with MICA or MICB. Such soluble molecules may have value not only in functional studies, but may also be useful in blocking T-cell recognition of MICA or MICB. The soluble molecules may also be exploited to derive minimal peptides or other agents that have powerful effects in blocking T-cell function. Further, soluble peptides may also be useful in adoptive immunotherapy.

D. Purification of MICA, MICB and Related Polypeptides

Within certain embodiments expression vectors are employed to express various genes to produce large amounts of MICA and/or MICB polypeptide product, MIC polypeptide binding agents, detection agents, or any other proteinaceous composition for use with the invention, which can then be purified. A use for a purified protein or peptide is, for example, to vaccinate animals to generate antisera or monoclonal antibody with which further studies may be conducted. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are required. The conditions for the use of a number of dominant drug selection markers for establishing permanent, stable cell clones expressing the proteinaceous products are also required, as is an element that links expression of the drug selection markers to expression of the polypeptide.

In certain embodiments of the invention, it will be desirable to produce functional MICA or MICB polypeptide, MIC polypeptide binding agents, detection agents, or variants thereof. Protein purification techniques are well known to those of skill in the art. These techniques tend to involve the fractionation of the cellular milieu to separate the MICA or/and MICB or related polypeptides from other components of the mixture. Having separated MICA or/and MICB and related polypeptides from the other plasma components, the MICA or/and MICB or related polypeptide sample may be purified using chromatographic and electrophoretic techniques to achieve complete purification. Analytical methods particularly suited to the preparation of a pure peptide are ion-exchange chromatography, exclusion chromatography; polyacrylamide gel electrophoresis; isolectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or β-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "–fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed elsewhere in the specification.

E. Synthetic Polypeptides

The present invention also describes the synthesis of peptides that bind to MIC proteins. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979). Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

F. Expression of Proteins from cDNA

The cDNA species specified in SEQ ID NO:1 and SEQ ID NO:3 may be expressed as peptide or protein, as well as any other proteinaceous compound discussed herein, such as a MIC polypeptide binding agent or a detection agent. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

Both cDNA and genomic sequences are suitable for eukaryotic expression, as the host cell will generally process the genomic transcripts to yield functional mRNA for translation into protein. In addition, it is possible to use partial sequences for generation of antibodies, which will be described later in the specification, against discrete portions of a gene product, even when the entire sequence of that gene product remains unknown. Computer programs are available to aid in the selection of regions which have potential immunologic significance. For example, software capable of carrying out this analysis is readily available commercially from MacVector™ (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with the present invention one would prepare an expression vector that comprises one of the MIC encoding nucleic acids or the nucleic acids that encode the binding agents of MIC, under the control of, or operatively linked to, one or more promoters. To bring a coding sequence "under the control of a promoter", one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized. In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt-cells, respectively. Also, antimetabolite resistance may be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

In the present embodiment of the invention, the MIC proteins encoding nucleic acids of the present invention may be "overexpressed", ie., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

III. Antibodies and Immunoassays

In some embodiments of the present invention, the use of binding agents that are immunoreactive with MICA, MICB, both MICA and MICB or any portion thereof is contemplated. These binding agents may be directed to soluble MIC. Any of the discussion regarding proteinaceous compositions may be applied to antibodies as well.

The amino acid sequence of cell surface MIC is the same as that of soluble or shedded MIC. Global or regional differences in the protein conformation or accessibility of cell surface MIC compared to soluble MIC are contemplated. Therefore, the antibodies designed and directed towards the soluble MIC may not bind or may bind weakly with the MIC proteins bound to the surface of tumor cells. This may result in detecting only the soluble MIC polypeptides. The detection of cell-surface bound MIC may be achieved by cell staining procedures such as immunofluorescence or other techniques as are well known to a person of ordinary skill in the art.

In other embodiments, the use of binding agents for NKG2D is contemplated. It is contemplated that soluble MIC may be detected by assaying for NKG2D. The decreased level of NKG2D is indicative of the presence of a soluble MIC polypeptide. Binding agents include polyclonal or monoclonal antibodies and fragments thereof In a preferred embodiment, an antibody is a monoclonal antibody. The following monoclonal antibodies of the present invention were prepared against MICA (2C10 and 3H5) and against MICA and MICB (6D4 and6G6), Such antibodies may form part of an immunodetection kit as described herein below.

An antibody of the present invention may be a bispecific antibody that is capable of recognizing both MICA and MICB. Multispecificity is a phenomenon that defines the ability of a single antibody molecule to combine with different antigens. Although a single antibody molecule has a unique three dimensional structure it can combine with the inducing antigenic determinant, determinants with similar structures (cross-reacting antigens), and perhaps even determinants with quite disparate structures. A stable antigen-antibody complex will result whenever there is a sufficient number of short-range interactions regardless of the fit. Within the antigen-combining site, a lack of fit in one region can be compensated for by increased binding elsewhere.

An antibody of the present invention may bind to more than one epitope from the same soluble MIC polypeptide. It may also bind to at least one epitope from MICA and at least one epitope from MICB.

Means for preparing and characterizing antibodies are well known in the art (See, e.g., Harlow and Lane, 1988). More specific examples of monoclonal antibody preparation are given in the examples below. Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Where the embodiment involves the use of an antibody that recognizes SEQ ID NO: 2 or SEQ ID NO: 4 consideration must be given to the mechanism by which the antibody is introduced into the cell cytoplasm. This can be accomplished, for example, by providing an expression construct, as described in the earlier section, that encodes a single-chain antibody version of the antibody to be provided. Alternatively, it is possible to present a bifunctional antibody, where one antigen binding arm of the antibody recognizes SEQ ID NO: 2 or SEQ ID NO: 4 and the other antigen binding arm recognizes a receptor on the surface of the cell to be targeted. Another alternative that may be possible is to generate two sets of antibodies specific to SEQ ID NO: 2 or SEQ ID NO: 4 individually but administer them in a combination.

Antibodies, both polyclonal and monoclonal, specific for the peptides or proteins of the present invention may be prepared using conventional immunization techniques, as will be generally known to those of skill in the art. A composition containing antigenic epitopes of the compounds of the present invention can be used to immunize one or more experimental animals, such as a rabbit, a mouse, a rat, a hamster, a guinea pig, a goat, a pig a horse etc., which will then proceed to produce specific antibodies against the compounds of the present invention. Polyclonal antisera may be obtained, after allowing time for antibody generation, simply by bleeding the animal and preparing serum samples from the whole blood.

It is proposed that the polyclonal and monoclonal antibodies of the present invention will find useful application in standard immunochemical procedures, such as ELISA and Western blot methods and in immunohistochemical procedures such as tissue staining, as well as in other procedures which may utilize antibodies specific to MICA or MICB related antigen epitopes. For example, such antibodies may be employed in antibody cloning protocols to obtain cDNAs or genes encoding MICA, MICB or related proteins. They may also be used in inhibition studies to analyze the effects of MICA or MICB related peptides in cells or animals. Antibodies to MICA or MICB related antigen will also be useful in immunolocalization studies to analyze the distribution of soluble MICA or MICB or related peptides in various test samples such as sputum, tears, blood, plasma, spinal fluid, semen, lymphatic fluid, urine, stool, pleural effusion and ascites. In order to determine to determine the cellular or tissue-specific distribution of the MICA or MICB related peptide during various cellular events under different physiological conditions, cell staining methods are preferred. A particularly useful application of such antibodies is in purifying native or recombinant MICA or MICB related peptide, for example, using an antibody affinity column. The operation of all such immunological techniques will be known to those of skill in the art in light of the present disclosure.

A. Preparation of Monoclonal Antibodies

Monoclonal antibodies (MAbs) may be readily prepared through use of well-known techniques, such as those exemplified in U.S. Pat. No. 4,196,265. Typically, this technique involves immunizing a suitable animal with a selected immunogen composition, e.g., a purified or partially purified MICA or MICB protein, polypeptide or peptide or cell expressing high levels of MICA or MICB. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^6$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (RPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. MAbs produced by either means may be further purified, if desired, using filtration, centrifugation and various chromatographic methods such as HPLC or affinity chromatography.

The monoclonal antibodies specific to the particular MICA or MICB alleles may be utilized in other useful applications. For example, their use in immunoabsorbent protocols may be useful in purifying native or recombinant MICA or MICB isoforms or variants thereof.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

The antibodies may also be used in conjunction with both fresh-frozen and/or fornalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et a., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar, pelleting; cooling in ice water to harden the agar, removing the tissue/agar block from the tube; infiltrating and/or embedding the block in paraffin; and/or cutting up to 50 serial permanent sections.

B. Labeling of Antibodies

It is further contemplated that these antibodies may be labeled. While antibodies are discussed below, it is contemplated that any detection reagent and/or binding agent of the invention may be labeled as described herein. A label is defined as any moiety that may be detected in an assay. A detection agent is a compound that allows for the detection and/or isolation of another compound, such as a compound to which the detection agent binds. A detection agent may employ a label or it may be unlabeled. Alternatively, a first detection agent may be unlabeled yet bind a second detection agent that is labeled. Non-limiting examples of labels that have been conjugated to detection agents such as antibodies include enzymes, radiolabels, haptens, fluorescent labels, phosphorescent molecules, chemiluminescent molecules, chromophores, luminescent molecules, photoaffinity molecules, colored particles or ligands, such as biotin. The examples that involve detection by color are generally understood to be colorimetric labels or detection reagents. Herein, "label" and "detection reagent" are used interchangeably. "Detectable labels" are compounds and/or elements that can be detected due to their specific functional properties, and/or chemical characteristics, the use of which allows the antibody to which they are attached to be detected, and/or further quantified if desired.

The monoclonal conjugates of the present invention may be prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99m}$Tc. Radioactively labeled monoclonal antibodies of the present invention are produced according to well-known methods in the art.

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241.

Yet another known method of site-specific attachment of molecules to antibodies comprises the reaction of antibodies with hapten-based affmity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody ( U.S. Pat. Nos. 4,472,509 and 4,938, 948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

It also contemplated that conjugates may be multimeric. A polypeptide conjugate multimer refers to a proteinaceous compound that contains at least two amino acid regions, wherein the regions are from different organisms or polypeptides and wherein each region is attached to another region, covalently or non-covalently; this is described in U.S. Pat. No. 5,976,546.

In the present invention, it is further contemplated that the antibody may be linked to a second antibody which may bind to a different epitope than the first antibody. This epitope may be either more than one from the same soluble MIC polypeptide or at least one epitope from MICA and at least one epitope from MICB. Further, this antibody, may be labeled as described above.

In further embodiments, it is also contemplated that the antibody to MIC polypeptide is unlabelled but is detected using a detecting agent that may also be an antibody. The antibody that binds to MIC is termed as a first detection agent. The detection agent that is used to detect the anti-MIC antibody is termed as a second detection antibody. This antibody may be biotinylated and may bind to the Fc region of the first detection agent, i.e, the antibody against the MIC polypeptide. The second detecting agent may further be linked to another detecting agent which may also be an antibody that comprises a streptavidin and a label. The label may be of any kind as described above. In some embodiments the first antibody may be linked to a solid support such as nitrocellulose, nylon or combinations thereof.

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509). The imaging moieties used can be paramagnetic ions; radioactive isotopes; fluorochromes; NM-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

a. Linkers/Coupling Agents

The MICA and MICB or NKG2D binding agents of the present invention may be linked to various labels, as described above, via a biologically-releasable bond, such as a selectively-cleavable linker or amino acid sequence. For example, peptide linkers that include a cleavage site for an enzyme preferentially located or active within a particular environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Amino acids such as selectively-cleavable linkers, synthetic linkers, or other amino acid sequences may be used to separate a compounds from one another.

Additionally, while numerous types of disulfide-bond containing linkers are known that can successfully be employed to conjugate compounds, such as an antibiotic to a polypeptide or a label to a polypeptide, certain linkers will generally be preferred over other linkers, based on differing pharmacologic characteristics and capabilities.

b. Biochemical Cross-linkers

The joining of any of the above components to MIC specific antibodies will generally employ the same technology as developed for the preparation of immunotoxins.

Cross-linking reagents are used to form molecular bridges that tie together functional groups of two different molecules, e.g., a stablizing and coagulating agent. To link two different proteins in a step-wise manner, hetero-bifunctional cross-linkers can be used that eliminate unwanted homopolymer formation. Examples of hetero-bifunctional cross-linkers are presented in Table 2.

TABLE 2

HETERO-BIFUNCTIONAL CROSS-LINKERS

| Linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It can therefore be seen that a MIC binding agent will generally have, or be derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking.

The spacer arm between the two reactive groups of cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed to conjugate binding agents. Linkers that contain a disulfide bond that is sterically hindered may prove to give greater stability in vivo, preventing release of the targeting peptide prior to reaching the site of action. These linkers are thus one group of linking agents.

Once conjugated, the polypeptide generally will be purified to separate the conjugated from unconjugated compounds and from other contaminants. A number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation.

In addition to chemical conjugation, a purified proteinaceous compound may be modified at the protein level. Included within the scope of the invention are protein fragments or other derivatives or analogs that are differentially modified during or after translation, for example by glycosylation, acetylation, phosphorylation, amidation, derivatization by known protecting/blocking groups, and proteolytic cleavage. Any number of chemical modifications may be carried out by known techniques, including but not limited to specific chemical cleavage by cyanogen bromide, trypsin, chymotrypsin, papain, V8 protease, $NABH_4$; acetylation, fonnylation, farnesylation, oxidation, reduction; metabolic synthesis in the presence of tunicamycin.

It is contemplated that any proteinaceous conjugate discussed in this section may, if appropriate, be prepared recombinantly. It may be noted that the above discussion may also be extended to NKG2D marker protein.

C. Immunoassays

As mentioned earlier, MIC in its soluble or bound form can be used as an important detection marker to determine the presence of cancer. The various situations where this type of detection may be employed are: where a subject does not reveal the presence of tumor nor does he possess any cancer symptoms but shows presence of shedded MIC which is indicative of the presence of tumor cells. It may also be employed in a situation where the tumor has been removed in a patient and an assessment of the level of soluble MIC is done to indicate how much more tumor needs to be removed or treated. Further, the presence of soluble MIC may also be useful in a long term treatment strategy where the patient is completely rid of tumor but needs to be constantly monitored for the recurrence of tumor. The presence of tumor cell bound MIC is more a diagnostic method to indicate the presence of tumor cells. In the presence of tumor cell-surface bound MIC, a combined assay to detect both soluble and cell-surface bound MIC may be carried out. This application may enable one to determine the total amount of MIC present in a sample.

The antibodies of the present invention can be used in characterizing the MICA and MICB content of healthy and diseased tissues by detection of soluble MICA and/or MICB in samples such as serum. These antibodies may be bispecific to MICA and MICB. Alternatively a combination of antibodies specific to MICA and MICB exclusively may also be used in the assays. The antibodies, as mentioned earlier, may also be raised and directed against NKG2D. Yet another alternative, as mentioned earlier, would be to detect the presence of both soluble and cell-surface bound MIC.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and other immunoassay techniques well known to those of ordinary skill in the art.

In one exemplary ELISA, antibodies binding to the MIC proteins are immobilized onto a selected surface exhibiting protein affinity, such as a well in a polystyrene microtiter plate. Then, a test composition suspected of containing the soluble MIC polypeptides, such as a clinical sample, is added to the wells. After binding and washing to remove non-specifically bound immunecomplexes, the bound antigen may be detected. Detection is generally achieved by the addition of a second antibody specific for the binding agent which, in the present invention, may be an antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the MIC antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the cancer marker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows: In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand. "Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate.

Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

It may be noted that all the above techniques may also be extended to detect antibodies against NKG2D.

The ELISA technique for analysis and quantification of proteins, especially soluble proteins is well known to a person of ordinary skill in the art (Fernandez et al., 2001; Kotzsch et al, 2000; Jensen et al., 2000; Kuroiwa et al., 2000; Bank et al, 1999; Hornig et al., 1999; Tak et al., 1999; Honda et al., 1992; Nygaard et al., 1998; Taylor et al., 2001; Soares et al., 2001).

The sandwich ELISA technique, as mentioned earlier, is also a very useful tool for the detection of soluble peptides. In this technique, specific antibodies are attached to the surface of a sensitive solid plate, then exposed to the sample thought to contain antigen. Any unbound material is washed away and then an enzyme-labeled specific antibody to the antigen is added, allowed to react, and then the washing step is repeated. In the present invention the antibody may be the monoclonal antibodies against MICA or MICB such as 2C10, 6D4, 6G6, 3H5 or an antibody specific to NKG2D. A colorless substrate is added to the plate, and if antigen was present in the original sample, the enzyme attached to the second antibody binds to the antigen and converts the substrate into a colored product. The amount of antigen present in the original sample is determined by quantification of the color produced. The sandwich ELISA technique is well known to a person with ordinary skill in the art and is may be found in references such as Perlmann et al., 1994; Crowther, J. R., 1995, Harlow et al., 1988.

The compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are imimunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

The use of lectins for the detection of glycosylated MIC may be employed and such techniques are well known to a person of ordinary skill in the art and may be found in the following references (Gabius et al., 1998; Makita et al., 1992; Rousseau et al., 1997). In further embodiments, it is also contemplated that the detection of soluble MIC and cell-surface bound MIC may be carried out by a combination of techniques each specific for their detection. For example, a combination of antibodies specific to soluble MICA or MICB or both and cell staining methods specific to cells bearing MICA or MIC B or both. This method will enable one to quantify the total amount of MICA or MICB or both present in the body.

D. Immunodetection Kits

In still further embodiments, the present invention concerns immunodetection kits for use with the immunodetection methods described above. The antibodies to MICA or MICB or both or antibodies to NKG2D may be employed to detect encoded proteins or peptides such as MICA and/or MICB or NKG2D respectively, either or both of such components may be provided in the kit. The immunodetection kits will thus comprise, in suitable container means, a first antibody that binds to an encoded protein or peptide, and an immunodetection reagent or a combination of antibodies that bind to MICA or MICB or both or NKG2D.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

Other variation of the kits described above may include any other MIC polypeptide binding agent, such as an NKG2D peptide or polypeptide that specifically binds to MICA, MICB, or both. The polypeptide binding agent may be labeled or the kit may include instructions and/or reagents for labeling the binding agent.

IV. Nucleic Acid Compositions

The present invention contemplates the use of a variety of proteinaceous compositions, and their corresponding nucleic acids. The present embodiment of the invention contemplates the use of nucleic acid complementary at least to a portion of the NKG2D transcript to detect the levels of NKG2D, which in turn will determine the levels of soluble MIC polypeptides. A decreased level of NKG2D is indicative of the presence of a soluble MIC polypeptide. The amplification of NKG2D may also be used to detect levels of NKG2D.

The term "nucleic acid" is well known in the art. A "nucleic acid" as used herein will generally refer to a molecule (ie., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

In one embodiment, the nucleic acid sequences complementary to at least a portion of the nucleic acid encoding the NKG2D marker proteins will find utility as hybridization probes. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA done by the hybridization of the target DNA to that single probe in the mixture which is its complete complement (Wallace et al., 1981). The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. These nucleic acids may be used, for example, in diagnostic evaluation of tissue samples or employed to clone full length cDNAs or genomic clones corresponding thereto. In certain embodiments, these probes consist of oligonucleotide fragments. Such fragments should be of sufficient length to provide specific hybridization to a RNA or DNA tissue sample. The sequences typically will be 10-20 nucleotides, but may be longer. Longer sequences, e.g., 40, 50, 100, 500 and even up to full length, are preferred for certain embodiments.

Various probes can be designed around the above nucleotide sequences encoding the NKG2D marker. The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C.

In certain embodiments, it will be advantageous to employ nucleic acid sequences complementary to those encoding the NKG2D protein of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In particular embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.).

Following washing of the hybridized surface to remove non-specifically bound probe molecules, hybridization is detected, or even quantified, by means of the label. Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772.

A partial sequence may be used to identify a structurally-related gene or the full length genomic or cDNA clone from which it is derived. Those of skill in the art are well aware of the methods for generating cDNA and genomic libraries which can be used as a target for the above-described probes (Sambrook et al., 1989).

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid. The nucleic acids as listed above may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032 or via deoxynucleoside H-phosphonate intermediates as described by U.S. Pat. No. 5,705,629. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244.

A non-limiting example of an enzymatically produced nucleic acid include one produced by enzymes in amplification reactions such as PCR™ (see for example, U.S. Pat. No. 4,683,202 and U.S. Pat. No. 4,682,195), or the synthesis of an oligonucleotide described in U.S. Pat. No. 5,645,897. A non-limiting example of a biologically produced nucleic acid includes a recombinant nucleic acid produced (ie., replicated) in a living cell, such as a recombinant DNA vector replicated in bacteria (see for example, Sambrook et al. 1989). A nucleic acid may be purified on polyacrylamide gels, cesium chloride centrifugation gradients, or by any other means known to one of ordinary skill in the art (see for example, Sambrook et al., 1989).

Screening procedures that rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

V. Cancer Therapies

Embodiment of the invention include treatment of cancer in a patient where the sample of a subject is screened for the presence of MIC proteins, and if positive for cancer, the patient is treated with a cancer therapy. A wide variety of cancer therapies, known to one of skill in the art, may be used for the treatment of cancer.

The various therapies that are contemplated as a part of the present invention are cancer therapies, including radiotherapy, chemotherapy, immunotherapy, gene therapy, hormonal therapy, and/or local heat therapy. Thus, one can use one or several of the standard cancer therapies existing in the art.

A. Radiotherapeutic Agents

Radiotherapeutic agents and factors include radiation and waves that induce DNA damage for example, $\gamma$-irradiation, X-rays, UV-irradiation, microwaves, electronic emissions, radioisotopes, and the like. Therapy may be achieved by irradiating the localized tumor site with the above described forms of radiation.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

B. Chemotherapeutic Agents

Agents that affect DNA function are defined as chemotherapeutic agents, for example, agents that directly cross-link DNA, agents that intercalate into DNA, and agents that lead to chromosomal and mitotic aberrations by affecting nucleic acid synthesis. Some examples of chemotherapeutic agents include antibiotic chemotherapeutics such as, Doxorubicin, Daunorubicin, Mitomycin (also known as mutamycin and/or mitomycin-C), Actinomycin D (Dactinomycin), Bleomycin, Plicomycin. Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. And other agents for example, Cisplatin (CDDP), Carboplatin, Procarbazine, Mechlorethamine, Camptothecin, Ifosfamide, Nitrosurea, Etoposide (VP16), Tanoxifen, Raloxifene, Estrogen Receptor Binding Agents, Gemcitabien, Navelbine, Farnesyl-protein transferase inhibitors, Transplatinum, 5-Fluorouracil, and Methotrexate, Temazolomide (an aqueous form of DTIC), or any analog or derivative variant of the foregoing.

C. Immunotherapy

Immunotherapeutics, generally, rely on the use of immune effector cells and molecules to target and destroy cancer cells. The immune effector may be, for example, an antibody specific for some marker on the surface of a tumor cell. Some common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. Immune stimulating molecules may be provided as immune therapy: for example, cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with proteinaceous compositions that act as targeting agents against tumor markers will enhance anti-tumor effects. Thus one may use (i) Passive Immunotherapy which includes: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow; and/or (ii) Active Immunotherapy wherein an antigenic peptide, polypeptide or protein, or an autologous or allogenic tumor cell composition or "vaccine" is administered, generally with a distinct bacterial adjuvant (Ravindranath & Morton, 1991) and/or (iii) Adoptive Immunotherapy wherein the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

D. Gene Therapy

In yet another embodiment, the treatment is a gene therapy in which a therapeutic polynucleotide is administered to a patient with cancer Delivery of a vector encoding a targetting agent against a tumor marker polypeptide in conjunction with a second vector encoding one of the following gene products will have a combined anti-hyperproliferative effect on target tissues. Alternatively, a single vector encoding both genes may be used. A variety of proteins are encompassed within the invention, some of which are described elsewhere in the specification under the sections: Inducers of cellular proliferation, inhibitors of cellular proliferation, regulators of programmed cell death, and other agents.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100-1000, or up to $1\times10^4$, $1\times10^5$, $1\times10^6$, $1\times10^7$, $1\times10^8$, $1\times10^9$, $1\times10^{10}$, $1\times10^{11}$, or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass, or solid tumor, may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

The method of treating cancer includes treatment of a tumor as well as treatment of the region near or around the tumor. In this application, the term "residual tumor site" indicates an area that is adjacent to a tumor. This area may include body cavities in which the tumor lies, as well as cells and tissue that are next to the tumor.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

VI. Therapies for Autoimmune Diseases and Conditions

An autoimmune disease or condition is characterized by an underlying defect in which there is an immune response against the body's own organs and/or tissues. There are believed to be at least 80 such conditions and diseases, which include, but are not limited to, the following: Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfimction Syndrome (CFIDS), Chronic Inflammatory Demyelinating Polyneuropathy, Churg-Strauss Syndrome, Cicatricial Pemphigoid, CREST Syndrome, Cold Agglutinin Diseass, Crohn's Disease, Discoid Lupus, Essential Mixed Cryoglobulinemia, Fibromyalgia-Fibromyositis, Graves' Disease, Guillain-Barré, Hashimoto's Thyroiditis, Idiopathic Pulmonary Fibrosis, Idiopathic Thrombocytopenia Purpura (ITP), IgA Nephropathy, Insulin-dependent Diabetes, Juvenile Arthritis, Lichen Planus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis (RA), Sarcoidosis, Scleroderma, Sjögren's Syndrome, Stiff-Man Syndrome, Systemic Lupus Erythematosus (SLE), Takayasu Arteritis, Temporal Arteritis/Giant Cell Arteritis, Ulcerative Colitis, Uveitis, Vasculitis, Vitiligo, and Wegener's Granulomatosis. Methods and compositions of the invention are specifically contemplated for use with respect to RA.

Medications or therapies that slow or suppress the immune system response in an attempt to stop the inflammation involved in the autoinmmune attack are called immunosuppressive medications. These drugs include corticosteroids (prednisone), methotrexate, cyclophosphamide, azathioprine, and cyclosporin Cox-2 inhibitors, corticosteroids such as prednisone,

EXAMPLES

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods for Example 2

Assay of Soluble MIC

For the assays, serum and pleural effusion samples were screened by ELISA using different pairs of anti-MIC mAbs with non-competing binding specificities (α1α2 or αα3 domain epitopes (Groh et al. Proc. Natl. Acad. Sci. USA 93: 12445-12450, 1996; Groh et al. Science 279: 1737-1740, 1998). For antigen capture and detection, ELISA plates were coated with selected capture mAbs, washed and blocked following standard procedures, incubated with serial dilutions of sample and treated with biotinylated detection mAbs. Washed plates were incubated with streptavidin-HRP, washed and reactions developed with tetramethyl-benzidine substrate. In parallel, already available purified recombinant sMICA were used to calibrate the assays.

ELISA Technique

Figure 2:
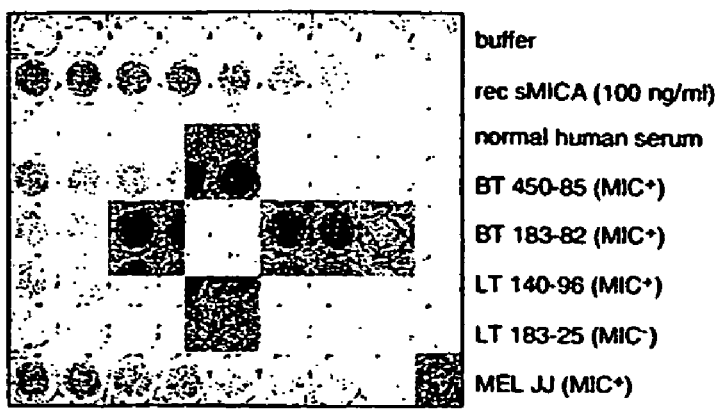
FIG. 2A. ELISA for detection of soluble MIC in body fluids from cancer patients. Horizontal wells represent continuous 1:2 sample dilutions from left to right. Lane 1: Sample buffer only. Lane 2: Titration of purified recombinant soluble MICA (100 ng/ml in left starting well) in sample buffer. Lane 3: Normal human serum. Lanes 4-8: Titration of serum samples from patients with tumors that were positive (BT 450-85, BT 183-82, LT 140-96, MEL JJ) or negative (LT 183-25) for MIC expression by flow cytometry of freshly prepared tumor cell suspensions. BT, breast tumor; LT, lung tumor, MEL, melanoma.
FIG. 2B. Incubation of peripheral blood CD8 T cells with C1R cell transfectants expressing MICA resulted in downregulation of NKG2D.
FIG. 2C. Incubation of T cells with untransfected C1R cells had no effect. The Cd3 profiles are control stainings.
FIG. 2D. Cell bound soluble MICA was detected 1 hour after addition to T cells but was undetectable after 24 hours of incubation, indicating lack of interference with binding of the anti-NKG2D antibody (mAB 1D11).
FIG. 2E. Downregulation of NKG2D on CD8 T cells by Purified recombinant soluble MICA (100 ng/ml) in cell culture wells. Expression of CD3 was unaltered
Figure 2:
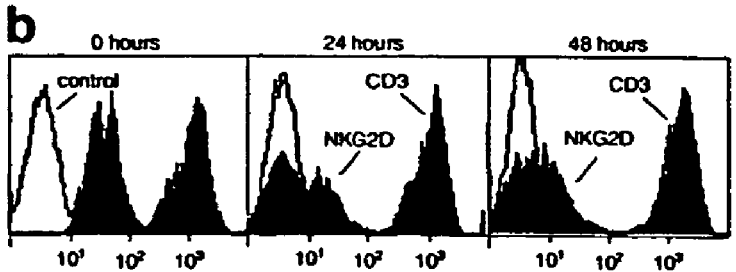
Figure 2:
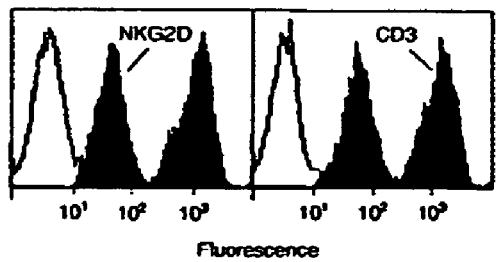
Figure 2:
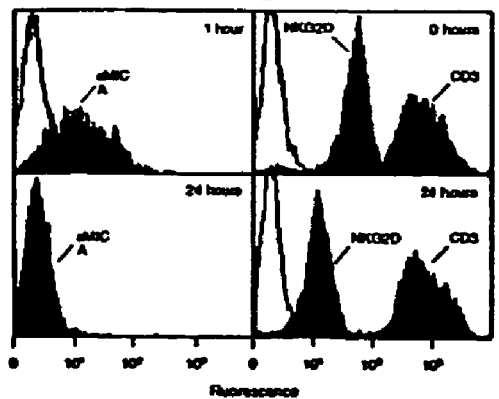

The inventors developed an ELISA technique for the detection of soluble MIC using three different pairs of selected mAbs with non-competing epitope specificities. Preliminary data showed the detection of purified recombinant MICA in ranges of 12.5-100 ng/ml PBS and 0.25-100 ng/ml negative control serum. Importantly, strong signals were obtained with serum samples from breast and lung tumors and a melanoma (FIG. 2; tumor specimens BT 450-85, BT 183-82, LT 140-96 and MEL JJ)). In these experiments, the inventors used mAb 6D4 (anti-MICA and -MICB) as the solid phase capture antibody on commercial ELISA plates and biotinylated mAb 2C10 (anti-MICA) and streptavidin-HRP for detection. This result supports the hypothesis that tumor associated MIC becomes systemically distributed into the circulation and has the capacity to downmodulate NKG2D on circulating lymphocytes.

Example 2

MIC is Shed from Tumor Cells

The inventors' results demonstrate that cell surface MIC alone, in the absence of TCR engagement, is sufficient to induce downmodulation of NKG2D on CD8 alpha beta T cells. Moreover, the repeatedly observed diminished expression of NKG2D not only on TIL but also on peripheral blood T cells from patients with MIC-positive tumors raises the question of whether this effect may be caused by soluble MIC shedded from tumor cells or whether it is due to transient contacts of circulating T cells with tumor cells (FIG. 1). The inventors show in FIG. 2 that this effect can be caused by soluble MIC shed from tumor cells.

The inventors investigated NKG2D expression on TIL and PBMC from patients with tumors that were positive or negative for MIC expression. The materials used included 27 paired tumors (5 colon, 5 ovarian, 7 lung, 6 breast carcinomas and 4 melanomas), TIL and peripheral blood samples. Freshly prepared tumor cell suspensions were tested for MIC expression by antibody staining and flow cytometry. The results showed that NKG2D expression was significantly diminished on about 30-50% of CD8 αβalpha beta T-cells among TIL and PBMC when the tumor cell suspensions were positive for MIC (FIG. 1). These results were not notably dependent on the proportions of tumor cells (10-100%) that expressed MIC. By contrast, the levels of NKG2D were normal when the tumor cells were negative for MIC (FIG. 1). Thus, these observations establish a link between tumor-associated expression of MIC and reduced expression of NKG2D.

Example 3

Materials and Methods Relevant to Embodiments Herein

Production of Monoclonal Antibodies.

RBF/DnJ mice (The Jackson Laboratories; Bar Harbor, Me.) were injected intraperitoneally three times at weekly intervals with $10^8$ C1R cells expressing MICA mRNA after stable transfection with MICA cDNA in RSV.5neo. After a final boost immunization, isolated splenocytes in suspension were fused with P3-X63Ag8.653 myeloma cells (Kearney et al., 1979) by standard polyethylene glycol treatment (Harlow and Lane, 1988). Hybridomas were grown in RPMI media with 10% of each CPSR-3 heat inactivated serum replacement controlled process type 3 (Sigma, St. Louis, Mo.) and Hybridoma Enhancing Supplement conditioned cultured medium from a murine lymphoma cell line (Sigma, St. Louis, Mo.) in 96-well plates under HAT (hypoxanthine aminopterin thymidine) selection on irradiated MRC-5 feeder cells (Harlow and Lane, 1988). Supernatants were differentially screened for specific reactivity with C1R-MICA cells versus untransfected C1R cells by indirect immunofluorescence and flow cytometry. Hybridomas from positive wells were subcloned twice. The isolated mAbs 56, 83 and 2C10 are of the IgG2a, IgG1 and IgG3 isotypes, respectively.

mAB 6D4 was generated by immunization of RBF/DnJ mice (Jackson Laboratories) with mouse LTK-MICA transfectants as described (Groh et al., 1996), and identified by screenings of hybridoma supernatants by indirect immunofluoresence stainings and flow cytometry of C1R, C1R-MICA and C1R-MICB transfectants. 6D4 was subcloned twice and is of the IgG1 isotype.

Labeling, Immunoprecipitation and Detection of MICA

For surface labeling, washed cells in phosphate-buffered saline (PBS) were biotinylated with Sulfo-NHS-LC-biotin (Pierce Chemical Co., Rockford, Ill.) (100 μg/ml) for 30 min at 4° C. and reactions quenched by addition of 25 mM lysine. $1-3 \times 10^7$ cells were lysed in 1 ml lysis buffer (1% Triton X-100, 50 mM Tris-OH (pH 7.4), 150 mM NaCl, 5 mM EDTA, 5 mM iodoacetamide, protease inhibitors). Protein in cleared supernatants was quantitated with a MicroBCA™ kit (Pierce, Chemical Co., Rockford, Ill.) and lysates were precleared using ULTRALINK-Protein A/G beads™ (Pierce Chemical Co.). MICA was precipitated with purified mAB 56 and protein A/G beads and immunocomplexes washed. Aliquots were treated with N-glycanase (PNGase F™, New England Biolabs Inc., Beverly, Mass.) as recommended by the manufacturer. Dissociated and dithiothreitol-reduced immunocomplexes were separated by SDS-polyacrylamide gel electrophoresis (SDS-PAGE) and electroblotted onto nitrocellulose using a Trans-Blot Semi-Dry Transfer Cell™ (Bio-Rad, Laboratories, Inc., Hercules, Calif.). After overnight incubation of membranes in PBS containing 10% dry nonfat milk, 0.05% TWEEN 20 and 0.02% Na-azide, they were repeatedly washed in TST (0.15 M NaCl, 10 mM Tris-OH (pH 7.4), 0.3% TWEEN 20) and reacted with avidin-horseradish peroxidase (Vector Laboratories Inc., Burlingame, Calif.) in TST (2.5 µg/ml) for 1 hour at 4° C. Membranes washed with TST were treated with ECL enhanced chemiluminescent reagent (Amersham, Life Science, Arlington Heights, Ill.) and exposed to X-ray film. For pulse-labeling and chase, $5 \times 10^6$ cells per time point were labeled with 0.5 mCi [$^{35}$S]methionine for 5 min. as described (Grandea et al., 1995). For chase, cells were spun through PBS with 10 mM methionine and resuspended in growth media for the indicated time periods. Cells were lysed, and MICA protein was precipitated using mAB 2C10 as described above. Isolated and denatured MICA was treated with endoglycosidase H (Endo H™, New England Biolabs) as recommended by the manufacturer and analysed by SDS-PAGE. Fixed gels were treated with AMPLIFY™ (Amersham) and dried for autoradiography.

Tissues and Immunohistology

Tissue samples from autopsies, biopsies or surgical specimens were embedded in TISSUE-TEK II™ O.C.T compound, a specimen matrix for cryostat sectioning (VWR Scientific Products, West Chester, Pa.) and frozen in liquid $N_2$-precooled methylbutane. Cryostat 4 µm sections mounted on poly L-lysine-coated slides were air-dried, fixed in cold acetone and overlaid with purified primary mAB appropriately diluted in staining buffer (PBS with 2% goat and 2% human serum, 0.1% TWEEN-20). After overnight incubation at 4° C., slides were washed and overlaid with fluorescein-conjugated goat F(ab')$_2$ anti-mouse IgG (Tago Inc., Burlingame, Calif.) diluted 1:150 in staining buffer. Coverslipped sections were examined by confocal immunofluorescence microscopy. For the double-stainings nuclei were visualized with propidium iodide. The epithelial desmosomal cadherin desmoglein-I was detected with biotinylated mAB DG3.10 (Schmidt et al., 1994) (Progen, Heidelberg, Germany) and Texas Red-conjugated streptavidin as the second layer. Autopsy tissue specimens included brain, heart, lung, thyroid, liver, kidney, skin, adrenal gland, placenta, tonsil and spleen and were obtained from Swedish Hospital (Seattle, Wash.). Gastric and small and large intestinal biopsy specimen were kindly provided by D. Levine (University of Washington Medical Center, Seattle, Wash.). Thymus specimens from corrective infant cardiac surgery were kindly provided by D. Hall and F. Lupinetti (Children's Hospital, Seattle, Wash.). For antibody staining and flow cytometry analysis, thymocyte suspensions were prepared by passing minced tissue through wire mesh. Peripheral blood mononuclear cells from randomly selected donors were isolated by density gradient centrifugation through Ficoll-Hypaque (Pharmacia).

Example 4

Materials and Methods for Example 5

Peripheral Blood Samples, Tissue Materials and Cell Preparations

Peripheral blood was obtained from 30 unrelated patients fulfilling the 1988 American College of Rheumatology criteria for RA and from 20 random healthy volunteers. Synovial tissues were obtained from 19 RA patients at the time of joint arthroplasty or by closed needle synovial biopsy. Peripheral blood and synovial tissue samples were from different patient populations. These activities were approved by local institutional review boards and all subjects gave written informed consent. Peripheral blood mononuclear cells (PBMC) were isolated by Ficoll-Hypaque density gradient centrifugation. CD4 T cells were purified from unseparated peripheral blood by negative selection using a RosetteSep (StemCell Technologies, Vancouver, BC) enrichment cocktail. NKG2D−CD4 T cells were isolated from purified CD4 T-cell populations with a BD FACSVantage cell sorter (BD Biosciences, San Diego, Calif.) following immunofluorescence staining with anti-NKG2D monoclonal antibody (mAb) 1D11 (Bauer et al., 1999) and phycoerythrin (PE)-goat anti-mouse immunoglobulin (Ig) F(ab')$_2$. For isolation of synovial cells, tissues were minced, partially digested with 0.3 mg/ml collagenase (Sigma, St. Louis, Mo.), pressed through a metal screen, and centrifuged through Ficoll-Hypaque.

Flow Cytometry and Immunohistochemistry

PBMC and synovial mononuclear cells were examined by two- or three-color flow cytometry using various combinations of anti-CD3, -CD4, -CD8, CD14, -CD56, -TCRγδ, -CD28, -CD45RA, or -CD45RO, (BD/Pharmingen, San Diego, Calif.) conjugated to either PE, fluorescein isothyocyanate (FITC), or PerCP. Binding of anti-NKG2D (1D11; Bauer et al., 1999) and anti-Ki-67 (BD/Pharmingen, San Diego, Calif.) was detected with PE- or FITC-goat anti-mouse Ig F(ab')$_2$. Biotinylated anti-MIC mAb 6D4 (Groh et al., 1998) was detected with streptavidin-FITC. For intracellular stainings, cells were permeabilized with 0.1% saponin for 10 min at 4° C. prior to antibody exposure. For immunohistochemistry stainings, 4-micron cryostat sections were made from synovial tissues embedded in OCT compound (Sakura Fine Technologies, Tokyo, Japan) and snap-frozen in liquid nitrogen. Sections were fixed in acetone, air dried, rehydrated in Tris-buffered saline (TBS), and blocked sequentially with 0.03% hydrogen peroxide, 25% normal goat serum, and 25% pooled human serum, all in TBS. Sections were incubated with anti-MIC mAb 6D4 (Gorh et al., 1998), anti-NKG2D mAb 1D11 (Bauer et al., 1999), anti-CD14, or isotype-matched IgG for 1 h at room temperature in a humid chamber. Antibody binding was detected using biotinylated secondary IgG and streptavidin-horse radish peroxidase (HRP) (Dako Corporation, Carpinteria, Calif.). Sections were counterstained with Harris' hematoxylin and mounted with gycergel (Dako Corporation).

Induction of NKG2D and Generation of T-Cell Clones and Synovial Fibroblast Cell Lines Peripheral blood CD4 T cells from healthy volunteers and CD4+NKG2D− T cells from RA patients were cultured in RPMI-1640, 10% fetal calf serum (FCS) and antibiotics with or without interleukin-15 (IL-15; 15 ng/ml), TNF-α (15 ng/ml), IL-10 (20 ng/ml), IL-12 (20 ng/ml), or IFN-γ (10 ng/ml) (R&D Systems, Minneapolis, Minn.) for up to 10 days. T cells were tested for NKG2D expression before and at various time points after cytokine exposure by flow cytometry. In some experiments, CD4 T cells were stimulated with solid-phase anti-CD3 (OKT3, 50 ng/ml; Orthobiotech, Raritan. N.J.). For generation of T-cell clones, CD4+NKG2D+ CD28− T cells were sorted from RA PBMC and synovial cell suspensions and seeded at 0.5 cells per well in 96-well round-bottom microtiter plates using a FACSVantage cell sorter. T cells were cultured with weekly restimulations with γ-irradiated allogeneic PBMC ($10^5$ cells/well) in RPMI-1640 supplemented with 8% FCS, 2% pooled human serum, antibiotics and IL-2 (50 IU/ml; Chiron, Emeryville, Calif.). RA synovial fibroblast cultures were established from cell suspensions prepared from two biopsies (see above) by adherence to tissue culture plates followed by removal of non-adherent cells. Adherent cells were cultured in DMEM supplemented with 10% FCS, 1 mM non-essential amino acids, 1 mM sodium pyruvate and antibiotics. After four passages, cultures were free of contaminating mononuclear cells and expressed high levels of MIC as confirmed by flow cytometry.

RNA Blot Hybridization

Total cellular RNA was extracted and purified from freshly isolated CD4 T cells and CD4 T cells cultured in the presence of cytokines using STAT-60 reagent (Tel-Test, Friendswood, Tex.). Gel electrophoresis and blot hybridization were standard procedures.

Cytotoxicity, Cytokine Release and T-Cell Proliferation Assays

T-cell cytolytic activity was tested in standard 4-h [$^{51}$Cr] release assays with labeled target cells that included the mouse mastocytoma P815 cell line for redirected lysis and MICA transfectants of the B-lymphoblastoid C1R cell line (Bauer et al., 1999). Redirected lysis was tested in the presence of anti-NKG2D (1D11) and anti-CD3 (OKT3) mAbs or isotype controls, each at a concentration of 2 μg/ml. Assays were done in triplicate and results scored according to the standard formula. In the cytokine release assays, resting (14 days after stimulation) T cells ($10^5$ per well) were stimulated with either solid-phase anti-CD3 with or without anti-NKG2D or control Ig as described (Groh et al., 2001), or with equal numbers of autologous or mismatched irradiated synovial fibroblasts. For blocking experiments, effector or stimulator cells were incubated with saturating amounts of anti-NKG2D, anti-MIC (mAb 6D4; 20) or control IgG 30 min prior to and throughout the co-culture. After 24 h, T-cell supernatants were collected from triplicate wells and pooled. The amounts of secreted IFN-γ and TNF-α were determined by commercial enzyme-linked immunosorbent assay (ELISA) with matched antibody pairs in relation to standard pairs (R&D Systems, Minneapolis, Minn.). T-cell proliferation was measured with resting T cells ($10^5$ cells per well) after activation with solid-phase mAb as described above. Cultures were pulsed with [$^3$H]thymidine on day 3 and collected after 12 h using a micromate cell harvester (Packard, Meridan, Conn.). Incorporated radioactivity was determined using Unifilter GF/C plates and a topcount (Packard).

ELISA of Soluble MICA and Modulation of NKG2D

Serum samples matched with MIC-positive synovial biopsies from RA patients were tested for the presence of soluble MICA by ELISA exactly as described (Groh et al., 2002). Modulation of NKG2D on peripheral blood CD4 T cells among PBMC from RA patients by soluble MIC containing RA sera (1:5 dilutions of sera coded RA-1, -2, and -3) in the presence or absence of neutralizing mAb against MIC (mAb 6D4; 20), IL-15 or TNF-α (1 μg/ml; R&D Systems, Minneapolis, Minn.) was examined after 48 h of incubation by staining with anti-CD4 and anti-NKG2D and flow cytometry (Bauer et al., 1999; Groh, et al., 2002). As a control experiment, T cells were exposed to the soluble MIC+ BT 450-85 serum from a breast cancer patient, which dowmnodulates NKG2D on CD8 T cells (Groh et al., 2002).

Example 5

NKG2D Stimulates Autoreactivity of CD4 T Cells Against Rheumatoid Arthritis Synoviocytes with Aberrant Expression of MIC CD4+CD28− T Cells from RA Patients Express NKG2D Peripheral blood lymphocytes (PBL) from 30 RA patients and 20 healthy volunteers were profiled for NKG2D expression by antibody staining and flow cytometry. The amounts and distribution of NKG2D among RA CD8 T cells, NK cells, and γδ T cells were similar to those recorded with the control PBL (inventors' data; Bauer et al., 1999). However, 5 to 40% (mean 11%) of RA CD4 T cells were positive for NKG2D whereas nearly all control CD4 T cells were negative (inventors' studies; Bauer et al., 1999). Whether NKG2D expression was associated with CD4+CD28− T cells was examined by multicolor flow cytometry. Consistent with previous observations, these T cells occurred among all RA but not normal PBL, at frequencies ranging from 3 to 50% (mean 12%) (Martens et al., 1997). With all RA PBL samples, NKG2D was preferentially expressed on CD4+CD28− T cells, with positive cell numbers ranging from 20 to 100%. In general, larger expansions of CD4+CD28− T cells correlated with disproportionally higher numbers of NKG2D+cells, suggesting an involvement of NKG2D in T-cell proliferation.

RA CD4+CD28− T cells occur at sites of tissue injury, including synovial joints and rheumatoid vasculitis (Schmidt et al., 1996; Namekawa, et al., 1998). As with circulating RA CD4 T cells, NKG2D was present on synovial tissue CD4 T cells, preferentially on those lacking CD28, whereas its expression on other lymphocyte infiltrates was unchanged. Thus, circulating and resident CD4 T cells from patients with RA frequently expressed NKG2D. Its main occurrence among the cytotoxic CD28− subset suggests that it may participate in autoimmune tissue damage. NKG2D was also present on some RA CD4+CD28+ T cells and was associated with a memory phenotype as indicated by CD45 isotype expression. It has been suggested that CD4+CD28− T cells may be derived from CD28+ memory T cells with replicative senescence (Vallejo et al., 2000; Warrington et al., 2001).

Induction of NKG2D on CD4 T Cells by IL-15 and TNF-α

Under normal conditions, the tissue distribution of the MIC ligands of NKG2D is limited to intestinal epithelium where intraepithelial CD8 T cells have diminished expression of NKG2D as a result of ligand-induced downmodulation (Groh et al., 1996; Groh et al., 2002; Roberts et al., 2001). However, NKG2D can be upregulated on these T cells by IL-15 (Roberts et al., 2001), which is prominent among the proinflammatory cytokines that are abundant in RA synovia (McInnes et al., 1996, 1997; Kurowska et al., 2002). Whether IL-15 was responsible for the aberrant expression of NKG2D on RA CD4 T cells was therefore tested. Normal PBL were cultured in the presence or absence of IL-15 for several days and surface NKG2D on lymphocyte subsets was monitored by flow cytometry. With CD8 T cells and NK cells, IL-15 had no effect on NKG2D being already expressed at maximum levels. However, NKG2D was progressively induced on CD4 T cells, with small positive populations (5-10% of CD4 T cells) appearing as early as 48 hours after addition of IL-15. Maximum induction was reached after 6 to 7 days of culture, with about 40% of CD4 T cells expressing NKG2D. Thereafter, NKG2D decreased gradually unless the culture was replenished with fresh IL-15. A similar but markedly accelerated induction of NKG2D was observed with sorted RA CD4+ NKG2D– T cells. Already after 24 hours, about 10 to 20% of the T cells expressed NKG2D, and the majority was positive after 3 days. As indicated by intracellular stainings of peTmeabilized cells, the more rapid appearance of surface NKG2D was likely due to redistribution of intracellular protein in a subpopulation of the RA CD4+NKG2D– T cells, whereas the delayed response was due to induction of mRNA.

As with IL-15, TNF-α is a key cytokine in the immunopathology of RA and induced NKG2D expression on CD4+ NKG2D– T cells among control and RA PBL. Both mediators were confirmed in all of 10 RA peripheral blood serum samples, at concentrations of 6.4-13.3 pg/ml (mean 8.2 pg/ml) and 16.5-52.2 pg/ml (mean 24.4 pg/ml), respectively. Exposure to other cytokines including IL-2 and IL-10, but not IL-12 and IFN-γ, resulted in less pronounced and variable induction of NKG2D. TCR complex stimulation with anti-CD3 transiently induced NKG2D on some CD4 T cells. Unlike the preferential association of NKG2D with CD4+ CD28– T cells in vivo, its induction on CD4 T cells appeared random in vitro. This was reminiscent of the restricted expression of CD94-NKG2A and CD94-NKG2C on activated effector T cells in vivo and the more random induction of these receptors by IL-15 or TCR triggering in vitro (14, 15, 29, 33).

Aberrant Expression of MIC in RA Synovium

To explore the significance of CD4 T cell expression of NKG2D in the immunopathology of RA, frozen sections of disease synovial tissue specimens were tested for the presence of MIC by immunohistochemistry using mAb 6D4, which is specific for MICA and MICB, and isotype-matched negative control antibody (20). As visualized by peroxidase substrate stainings, all tissue specimens contained numerous positive cells. Control stainings of cell suspensions derived from osteoarthritis tissue specimens gave negative results. MIC+ synoviocytes of spindle-shaped fibroblast-like and more rounded morphologies were distributed throughout the synovial lining and sublining areas and were often located close to, or interspersed with, lymphocytic aggregates. They were in close contact with NKG2D+ cells, which were scattered throughout synovial lining an d sublining areas and were present in organized lymphoid microstructures. Rheumatoid synovial hyperplasia consists of fibroblasts and activated macrophages. The former have features of immortalized transformed cells and proliferate aggressively (Krause et al., 2002), which can explain the induced expression of MIC (Groh et al., 1998). This was supported by two-color stainings of permeabilized synovial cell suspensions with antibodies against the nuclear Ki-67 proliferation marker and MIC. Analysis by flow cytometry revealed that the presence of MIC was strongly but not completely associated with expression of Ki-67. Thus, in accord with previous evidence obtained with fibrob last and epithelial cell lines (Groh et al., 1998), expression of MIC was induced in proliferating rheumatoid synoviocytes.

NKG2D Stimulates CD4+CD28– T-Cell Autoreactivity

CD4+CD28– T cells resemble NKT cells as they secrete large amounts of IFN-γ and express perforin and granzyme B, which confer cytotoxic capacity (Park et al., 1997; Namekawa, et al., 1998). To test the function of NKG2D, each of the five CD4+CD28–NKG2D+ T-cell clones from one RA synovial tissue specimen and two RA PBL samples were established. In antibody-dependent cytotoxicity assays, ligation of NKG2D did not induce redirected lysis of FcγR+ mouse mastocytoma P815 cells by any of the 15 T-cell clones although anti-CD3 was effective, thus confirming their cytotoxic capacity. Consistent with previous results obtained with antigen-specific CD8 αβ T cells (Groh et al., 2001), no cytotoxicity was scored against the C1R-MICA transfectant B-cell line. However, mAb crosslinking of NKG2D strongly augmented anti-CD3-triggered release of IFN-γ and TNF-α by all T-cell clones and stimulated T-cell proliferation. Thus, as with antigen-specific effector CD8 αβ T cells, NKG2D costimulated RA CD4+CD28– T cells (Groh et al., 2001). These results show that NKG2D contributes to the frequent expansion of these T cells in RA.

CD4+CD28– T cells are thought to promote the formation and maintenance of RA inflammatory lesions mainly through IFN-γ release. INF-γ perpetuates synoviocyte pathology, which is associated with secretion of TNF-α, IL-15, and tissue-injurious metalloproteinases by synovial fibroblasts and macrophages (Klimiuk et al., 1999). It was tested whether ligation of NKG2D by MIC+ RA synoviocytes could induce cytokine production by synovial CD4+CD28– NKG2D+ T-cell clones. T cells were stimulated with autologous or mismatched RA synoviocytes and release of INF-γ and TNF-α was measured in the presence or absence of anti-MIC or anti-NKG2D mAb. Cytokine release was stimulated by the autologous but not the allogeneic synoviocytes and was abrogated by anti-MIC mAb. Anti-NKG2D moderately superinduced cytokine production as previously found with antigen-specific CD8 T-cell clones (inventors' data; Groh et al., 2001).

TNF-α and IL-15 Counteract Downmodulation of NKG2D by Soluble MIC in RA Patient Serum Binding of MIC induces downmodulation of NKG2D, which may normally serve to prevent chronic T-cell stimulation and limit autoreactive by-stander T-cell activation in local tissue environments. Many epithelial tumors cause a systemic downmodulation of NKG2D by shedding of soluble MIC, which is presumably mediated by metalloproteinases (Groh et al., 2002; Salih et al., 2002). Since metalloproteinases are secreted by RA synoviocytes, we tested peripheral blood serum samples from RA patients for the presence of soluble MICA using an enzyme-linked immunosorbent assay (ELISA). Positive results were obtained with all of the 10 samples tested, which contained 2.7-30.6 ng/ml (mean 5.8 ng/ml) of soluble MICA. This raised the question of why NKG2D was expressed at high levels on RA CD4+CD28– T cells as well as on CD8+ T cells. As expected, incubation of RA patient PBMC with diluted serum from a breast tumor patient diminished NKG2D expression on CD4+NKG2D+ T cells because of the presence of soluble MICA. By contrast, RA patient serum had no effect. However, in the presence of neutralizing antibodies against TNF-α and IL-15, NKG2D was markedly reduced. Thus, the ligand-induced downmodulation of NKG2D was compensated in RA patients by the opposite effect of its cytokine-mediated induction.

The self-perpetuating pathophysiology in RA is caused by the interplay between lymphocytic infiltrates, synovial macrophages and fibroblasts and their products. Destruction of cartilage results from pannus invasion, which is composed of activated macrophages and proliferating fibroblasts. Both cell types secrete metalloproteinases and enzymes that degrade surrounding cartilage and extracellular matrix and produce inflammatory cytokines such as TNF-α and IL-15 (Feldman et al., 1996; Muller-Ladner et al., 1998). These activities are promoted by large amounts of CD4 T-cell infiltrate-derived IFN-γ, as indicated by T-cell depletion and IFN-γ reconstitution experiments (Klimiuk et al., 1999). This example show that substantial numbers of RA synovial and circulating CD4 T cells, which frequently lack CD28, express NKG2D and that its MIC ligands are induced on proliferating RA synoviocytes. Engagement of NKG2D by MIC costimulates CD4 T cell IFN-γ release and proliferation, thus demonstrating a critical role of this receptor-ligand interaction in disease progression for which soluble MIC serves as a useful prognostic indicator.

The occurrence of CD4+CD28− T cells in other autoimmune diseases such as Wegener's granulomatosis, ankylosing spondylitis and insulin-dependent diabetes mellitus (IDDM) (4-8) indicate a broader role of NKG2D and its ligands in autoimmune diseases.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,659,774
U.S. Pat. No. 4,683,195
U.S. Pat. No. 4,683,202
U.S. Pat. No. 4,816,571
U.S. Pat. No. 4,938,948
U.S. Pat. No. 4,959,463
U.S. Pat. No. 5,021,236
U.S. Pat. No. 5,141,813
U.S. Pat. No. 5,264,566
U.S. Pat. No. 5,428,148
U.S. Pat. No. 5,554,744
U.S. Pat. No. 5,574,146
U.S. Pat. No. 5,602,244
U.S. Pat. No. 5,645,897
U.S. Pat. No. 5,705,629
U.S. Pat. No. 5,843,663
U.S. Pat. No. 5,849,481
U.S. Pat. No. 5,849,486
U.S. Pat. No. 5,851,772
U.S. Pat. No. 5,900,481
U.S. Pat. No. 5,919,626
U.S. Pat. No. 5,976,546
Abbondanzo, *Ann Diagn Pathol,* 3(5):318-327, 1990.
Allred et al., *Arch Surg,* 125(1):107-13, 1990.
Atherton et al., *Biol Reprod,* 32(1):155-171, 1985.
Bahram and Spies, *Immunogenetics,* 43:230-233, 1996.
Bahram et al., *Proc. Natl. Acad. Sci. USA,* 91:6259-6263, 1994.
Bank et al., *J. Lab. Clin. Med.,* 134(6): 599-604, 1999.
Barany and Merrifield, The Peptides, Gross and Meienhofer, eds., Academic Press, New York, pp. 1-284 1979.
Bauer et al., *Science,* 285(5428): 727-729, 1999.
Bittner et al., *Methods in Enzymol.,* 153:516-544, 1987.
Brown et al. *Immunol Ser,* 53:69-82, 1990.
Campbell et al., *J. Mol. Biol.,* 180:1-19, 1984.
Capaldi et al., *Biochem. Biophys. Res. Comm.,* 76:425, 1977.
Colberre-Garapin et al., *J. Mol. Biol.,* 150:1, 1981.
Crowther, "Methods in Molecular Biology,", Vol. 42-ELISA: Theory and Practice, Humana Press, Totowa, N.J., 1995.
Dholakia et al., *J. Biol. Chem.,* 264(34):20638-20642, 1989.
EP 266,032
Feldman et al., *Cardiovasc. Res.,* 32(2):194-207, 1996.
Fernandez et al., *Microsc. Res. Tech.,* 52(5): 510-9, 2001.
Gabius et al., *Cancer,* 61(6):1125-31, 1998.
Gefter et al., *Somatic Cell Genet.,* 3:231-236, 1977.
Geraghty, D. E., *Curr. Opin. Immunol.,* 5:3-7, 1993.
Goding, In: *Monoclonal Antibodies: Principles and Practice,* 2d ed., Orlando, Fla., Academic Press, pp. 60-61, 65-66, 71-74, 1986.
Grandea et al., *Science* 270(5233):105-8, 1995.
Groh et al., *Proc. Natl. Acad. Sci. USA,* 93:12445-12450, 1996.
Groh et al, *Proc. Natl. Acad. Sci. USA,* 98:6879, 1998.
Groh et al., *Nat. Immun.,* 2(3): 255-60, 2001.
Groh et al., *Nature,* 419:734-738, 2002.
Grossberger and Parham, *Immunogenetics,* 36:166-174, 1992.
Harlow and Lane, Antibodies: A Laboratory Manual. Cold Spring Harbor Laboratory Press, Cold Spring harbor, NY, 553-612, 1988.
Honda et al., *J. Immunol.,* 148(7): 2175-80, 1992.
Hornig et al., *J. Immunol. Methods,* 226(1-2):169-177, 1999.
Houchins et al., *J. Exp. Med.,* 173:1017, 1991.
Jensen et al., *Mol. Med.,* 6(4):291-302, 2000.
Johnson et al., "Peptide Turn Mimetics" in *BIOTECHNOLOGY AND PHARMACY,* Pezzuto et al., Eds., Chapman and Hall, New York, 1993.
Kearney, et al., *J. Immunol.,* 123:1548-1550, 1979.
Khatoon et al., *Ann. Neurol,* 26(2):210-5, 1989.
King et al., *J. Biol Chem,* 264(17):10210-10218, 1989.
Klimiuk et al., *Clin. Immunol.,* 90:65-78, 1999.
Kluvins et al., *Ann. Clin. Lab. Sci.* 13:275-280, 1983.
Kohler and Milstein, *Eur. J. Immunol.,* 6:511-519, 1976.
Kohler and Milstein, *Nature,* 256:495-497, 1975.
Kotzsch et al., *Int. J. Oncol.,* 17(4):827-34, 2000.
Krause et al., *J. Immunol.,* 169:6610-6616, 2002.
Kuroiwa et al., *Hybridoma,* 19(2): 151-9, 2000.
Kurowska et al., *J. Immunol.,* 169:1760-1767, 2002.
Kyte and Doolittle, *J. Mol. Biol.,* 157(1):105-132, 1982.
Li et al., *Nat. Immunol.* 2:443-451, 2001.
Li et al., *Immunity,* 10: 577-584, 1999.
Lowy et al., *Cell,* 22:817, 1980.
Makita et al., *J. Biol. Chem.,* 267(8): 5133-8, 1992.
Martens et al., *Arthritis and Rheumatism,* 40:1106-1114, 1997.
McInnes et al., *Nat. Med.,* 2:175-182, 1996.

McInnes et al., *Nat. Med.,* 3:189-195, 1997.
Merrifield, *Science,* 232:341-347, 1986.
Muller-Ladner et al., *Curr. Opin. Rheumatol.,* 10:212, 1998.
Mulligan et al., *Proc. Nat'l Acad. Sci. USA,* 78:2072, 1981.
Nakamura et al., *J. Biol. Chem.,* 277:2687-2694, 2002.
Namekawa et al., *Arthritis and Rheumatism,* 41:2108-2116, 1998.
Namekawa et al., *J. Immunol.,* 165:1138-1145, 2000.
Nygaard et al., *Electrophoresis,* 19(11): 1989-97, 1998;
O'Hare et al., *Proc. Nat'l Acad. Sci. USA,* 78:1527, 1981.
Owens and Haley, *Biochem. Biophys. Res Commun.,* 142(3): 964-71, 1987.
Park et al., *Eur. J. Immunol.,* 27:1082-1090, 1997.
Perlmann and Perlmann, "Enzyme Linked Immunosorbent assay," In: *Cell Biology: A Laboratory Handbook.* San Diego, Calif., Academic Press, Inc., 322-328, 1994.
Pohl et al., *Cancer Detect. Prevent.* 6:7-20, 1983.
Potter and Haley, *Methods Enzymol,* 91:613-633, 1983.
Ravindranath and Morton, *Intern. Rev. Immunol.,* 7: 303-329, 1991.
Roberts et al., *J. Immunol.* 167:5527, 2001.
Rosenberg et al., *Ann. Surg.* 210(4):474-548, 1989.
Rosenberg et al., *N. Engl. J. Med.,* 319:1676, 1988.
Rousseau et al., J. Cell. *Biochem.,* 66(3):370-85, 1997.
Salih et al., *J. Immunol.,* 169:4098-4102, 2002.
Sambrook et al., In: *Molecular cloning,* Cold Spring Harbor Laboratory Press, Cold Spring Harbor, N.Y., 1989.
Santerre et al., *Gene,* 30: 147-156, 1984.
Schmidt et al., *Eur. J. Cell Biol.,* 65:229-245, 1994.
Schmidt et al., *J. Clin. Invest,*. 97:2027-2037, 1996.
Sikorska et al., *Cancer Detect. Prevent.,* 12:321-355, 1988.
Soares et al., *J. Immunol. Methods,* 249(1-2):199-205, 2001.
Spies et al., *Science,* 243:214-217, 1989.
Steinle et al., *Immunogenetics,* 53(4):279-87, 2001.
Stewart and Young, Solid Phase Peptide Synthesis, 2d. ed., Pierce Chemical Co. 1984.
Stroynowski, *Annu Rev Immunol,* 8:501-530, 1990.
Sultzeanu et al., *Adv. Cancer Res.* 44:1-42, 1985.
Szybalska et al., *Proc. Nat'l Acad. Sci. USA,* 48:2026, 1962.
Tak et al., *Clin. Exp. Immunol.,* 116(2): 366-70, 1999.
Tam et al., *J. Am. Chem. Soc.,* 105:6442, 1983.
Taylor et al., *J. Immunol. Methods,* 255(1-2):67-72, 2001.
Vallejo et al., *J. Immunol.,* 165:6301-6307, 2000.
Virji et al., *Cancer,* 38:105-126, 1988.
Wallace, et al., *Nucl. Acid Res.,* 9:879, 1981.
Warrington et al., *Arthritis and Rheumatism,* 44:13-20, 2001.
Wickens, M., *Trends Biochem. Sci.,* 15:277-281, 1990.
Wigler et al., *Cell,* 11:223, 1977.
Wigler et al., *Proc. Nat'l Acad. Sci. USA,* 77:3567, 1980.

The invention claimed is:

1. A method for modulating expression of NKG2D in a lymphocyte capable of expressing NKG2D comprising binding a tumor cell produced MIC polypeptide with a MIC polypeptide binding monoclonal antibody, wherein MIC suppressed NKG2D expression of the lymphocyte is increased.

2. The method of claim 1, wherein the antibody recognizes the α3 domain of MIC.

3. The method of claim 1, wherein the antibody is 6G6.

4. The method of claim 1, wherein the antibody recognizes the distal α1α2 domain of MIC.

5. The method of claim 4, wherein the antibody is 2C10, 6D4 or 3H5.

6. The method of claim 1, wherein the MIC polypeptide binding antibody binds soluble MIC.

7. The method of claim 1, wherein the MIC polypeptide binding antibody binds bound MIC.

8. The method of claim 1, wherein the cell is a T cell or natural killer cell.

9. A method comprising administering to a NKG2D expressing lymphocyte a neutralizing monoclonal antibody against tumor shed MIC, wherein MIC associated downmodulation of NKG2D in a the NKG2D expressing lymphocyte cell is inhibited.

10. A method for blocking downregulation of NKG2D on a lymphocyte comprising administering a MIC polypeptide binding monoclonal antibody that interacts with soluble MIC shed from a tumor cell, wherein the MIC polypeptide binding monoclonal antibody prevents shed MIC from binding NKG2D.

11. The method of claim 9, wherein the neutralizing antibody recognizes the α3 domain of MIC.

12. The method of claim 9, wherein the neutralizing antibody recognizes the distal α1α2 domain of MIC.

13. The method of claim 9, wherein the NKG2D expressing lymphocyte is a T cell.

14. The method of claim 10, wherein the NKG2D expressing lymphocyte is a T cell.

* * * * *

UNITED STATES PATENT AND TRADEMARK OFFICE
CERTIFICATE OF CORRECTION

PATENT NO. : 7,771,718 B2
APPLICATION NO. : 10/512181
DATED : August 10, 2010
INVENTOR(S) : Thomas Spies et al.

It is certified that error appears in the above-identified patent and that said Letters Patent is hereby corrected as shown below:

In column 1, line 12, delete "support grant" and insert --support under grant-- therefor.

Signed and Sealed this

Twenty-sixth Day of October, 2010

David J. Kappos
*Director of the United States Patent and Trademark Office*